US009949489B2

(12) United States Patent
Shatters et al.

(10) Patent No.: US 9,949,489 B2
(45) Date of Patent: Apr. 24, 2018

(54) METHODS FOR CONTROL OF HEMIPTERAN INSECT STYLET SHEATH STRUCTURE FORMATION

(71) Applicant: The United States of America, as Represented by the Secretary of Agriculture, Washington, DC (US)

(72) Inventors: Robert G. Shatters, Stuart, FL (US); Gary A. Luzio; John K. Morgan, Port Saint Lucie, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/140,666

(22) Filed: Apr. 28, 2016

(65) Prior Publication Data

US 2016/0316762 A1    Nov. 3, 2016

Related U.S. Application Data

(60) Provisional application No. 62/154,825, filed on Apr. 3, 2015.

(51) Int. Cl.
| | | |
|---|---|---|
| *A01N 63/02* | (2006.01) | |
| *A01N 31/02* | (2006.01) | |
| *A01N 31/08* | (2006.01) | |
| *A01N 37/44* | (2006.01) | |
| *A01N 43/16* | (2006.01) | |
| *A01N 43/90* | (2006.01) | |
| *A01N 59/16* | (2006.01) | |
| *A01N 63/04* | (2006.01) | |
| *A01N 65/08* | (2009.01) | |
| *A01N 65/40* | (2009.01) | |
| *A01N 65/44* | (2009.01) | |

(52) U.S. Cl.
CPC ............ *A01N 63/02* (2013.01); *A01N 31/02* (2013.01); *A01N 31/08* (2013.01); *A01N 37/44* (2013.01); *A01N 43/16* (2013.01); *A01N 43/90* (2013.01); *A01N 59/16* (2013.01); *A01N 63/04* (2013.01); *A01N 65/08* (2013.01); *A01N 65/40* (2013.01); *A01N 65/44* (2013.01); *C12Y 302/01004* (2013.01); *C12Y 304/16006* (2013.01); *C12Y 304/22002* (2013.01); *C12Y 304/22003* (2013.01); *C12Y 304/22004* (2013.01); *C12Y 304/22006* (2013.01)

(58) Field of Classification Search
None
See application file for complete search history.

(56) References Cited

U.S. PATENT DOCUMENTS

| | | | | |
|---|---|---|---|---|
| 5,985,273 A | * | 11/1999 | Reed ................... | A01N 37/46 424/94.63 |
| 2011/0239327 A1 | * | 9/2011 | Curtis ................. | A01N 37/46 800/279 |
| 2013/0305416 A1 | | 11/2013 | Baum et al. | |

FOREIGN PATENT DOCUMENTS

JP         2002-068917       *  3/2002

OTHER PUBLICATIONS

Morgan J. et al. Formation of Stylet Sheaths in Aere From Eight Species of Phytophagous Hemipterans . . . PLoS One 8(4)e62444.*
Alhaddad, Hasan, et al., "Comparative Behavioral and Protein Study of Salivary Secretions in *Homalodisca* spp. Sharpshooters (Hemiptera: Cicadellidae: Cicadellinae)" (2011) Physiology, Bochemistry, and Toxicology, 104(3):543-552.
Backus, Elaine A. et al., "Mechanisms of Hopperburn: An Overview of Insect Taxonomy, Behavior, and Physiology*", (2005) Annu. Rev. Entomol. 50:125-151.
Backus, Elaine A. et al., "Salivary enzymes are injected into xylem by the glassy-winged sharpshooter, a vector of Xylella fastidiosa", (2012) Journal of Insect Physiology 58:949-959.
Brennan, EB et al. "A new technique for studying the stylet tracts of homopteran insects in hand-sectioned plant tissue using light or epifluorescene microscopy", (2001) Botechnic & Histochemistry, 76(2); 59-66.
Carolan, James C. et al., "The secreted salivary proteome of the pea aphid Acyrthosiphon pisum characterised by mass spectrometry", (2009) Proteomics, 9:2457-2467.
Cherqui, Anas et al., "Salivary proteins of aphids, a pilot study on identification, separation and immunolocalisation", (2000) Journal of Insect Physiology, 46:1177-1186.
Cooper, William R. et al., "Salivary Proteins of Russian Wheat Aphid Hemiptera: aphididae)", (2010) Environmental Entomology. 39(1): 223-231.
Martinez De Llarduya, Oscar et al., "Aphid-Induced Defense Responses in Mi-1-Mediated Compatible and Incompatible Tomato Interactions", (2003) The American Phytopathological Society MPMI, 16(8):699-708.
Dejean, Alain, et al. "A new case of trophobiosis between ants and Heteroptera", (2000) Life Sciences 323: 447-454.
Forero, Dimitri, "The systematics of the Hemiptera", (2008) Revista Colobiana de Entomologia 34(1): 1-21.

(Continued)

*Primary Examiner* — Ralph J Gitomer
(74) *Attorney, Agent, or Firm* — David L. Marks; John D. Fado

(57) ABSTRACT

Compositions having at least one compound which inhibits the formation of Hemipteran stylet sheaths and/or degrades hemipteran style sheaths that have already been formed, and thus deters or blocks hemipteran insects from feeding on plants, especially agriculturally important plants and methods of use of such compositions are described. Such compositions can be applied onto plants by spraying, dripping, or other methods and/or can be applied to the soil for uptake by the roots. These compositions and methods prevent and/or reduce the transmission of vascular associated diseases (caused by hemipteran vector-borne pathogens) to plants.

18 Claims, 16 Drawing Sheets

(56) References Cited

OTHER PUBLICATIONS

Goggin, Fiona L., "Plant-aphid interactions: molecular and ecological perspectives", (2007) Current Opinion in Plant Biology, 10:399-408.
Gullan, Penny J. et al, "Sternorrhyncha", (2009) CH017.indd , 957-967.
Hattori, Makoto et al. "Molecular characterization and expression of laccase gense in the salivary glands of the green rice leafhopper, Nephotettix cincticeps (Hemiptera: Cicadellidae)", (2010) Insect Biochemistry and Molecular Biology, 40:331-338.
Kempema, Louisa A. et al. "*Arabidopsis* Transcriptome Changes in Response to Phloem-Feeding Silverleaf Whitefly Nymphs. Similarities and Distinctions in Responses to Aphids" (2007) Plant Physiology, (143):849-965.
Leopold, Roger A. et al. "Mouthpart morphology and stylet penetration of host plants by the glassy-winged shargpshoot, Homalodisca coagulata, (Homoptera: Cicadellidae)" (2003) Arthropod Structure & Development 32: 89-199.
Lloyd, Monte et al. "Xylem Feeding by Periodical Cicada Nymphs on Pine and Grass Roots, With Novel Suggestions for Pest Control in Conifer Plantations and Orchards", (1987) Ohio J. Science 87(3):50-54.
Bonani, J.P. et al. "Charcteriation of electrical penetrationgraphs of the Asian citrus psyllid, Diaphorina citri, in sweet orange seedlings", (2009) Entomologia Experimentalis et Applicata 134:35-49.
Madhusudhan, V.V. et al., "Mobility of salivary components as a possible reason for differences in the responses of alfalfa to the spotted alfalfa aphid and pea aphid" (1998) Entomologia Experimentalis et Applicata 86:25-39.
Miles, P.W. "Contact Chemoreception in Some Heteroptera, Including Chemoreception Internal To the Stylet Food CanaL" (1958) Journal Insect Physiology 2:338-347.
Miles, P.W. "The Salivary Secretions of A Plant-Sucking Bug, Oncopeltus Fasciatus (Dall.) (heteroptera: Lygaeidae)-I The Types of Secretion and Their Roles During Feeding", (1959) Journal Insect Physiology 3:243-255.
Miles, P.W. "The Salivary Secretions of A Plant-Sucking Bug, Oncopeltus Fasciatus (Dall.) (Heteroptera: Lygaeidae)-II Physical and Chemical Properties", (1960) Journal Insect Physiology 4:209-219.
Miles, P.W., "Studies on the Salivary Physiology of Plant Bugs: The Chemistry of Formation of the Sheath Material" (1964) Journal Insect Physiology 10:147-160.
Miles, P.W., "Studies on the Salivary Physiology of Plant-Bugs: The Salivary Secretions of Aphids", (1965) Journal Insect Physiology 11:1261-1268.
Miles, P.W., "Studies on the Salivary Physiology of Plant-Bugs: Transport From Haemolymph to Saliva", (1967) Journal Insect Physiology 13:1787-1801.
Miles, P.W. "Transport of Whole Protein Molecules from Blood to Saliva of a Plant-Bug" (1970) Experientia 26(6):611-612.
Miles., P.W. "The Saliva of Hemiptera" (1972) Advances in Insect Physiology (9):183-255.
Miles, P.W. et al., "Discharge by aphids of soluble secretions into dietary sources", (1991) Entomol. experimentalis Applicata 59:123-134.
Miles, Peter W. "Aphid saliva", (1999) Biological Reviews of the Cambridge Philosophical Society 74: 41-85.
Morgan, J. Kent et al. "Formation of Stylet Sheaths in aere (in air) from Eight Species of *Phytophagous hemipterans* from Six Families (Suborders Auchenorrhyncha and Stemorrhyncha)", (2013) PLOS One 8(4):1-11.
Ammar, El-Desouky et al. "Differences in Stylet Sheath Occurrence and the Fibrous Ring Sclerenchyma) between xCitroncirus Plants Relatively Resistant or Susceptible to Adults of the Asian Citrus Psyllid Diaphorina citri (hemiptera: Liviidae)" (2014) PLOS One 9(10): 1-10.
Sahayaraj, Kitherian et al. "Gross Morphology of Feeding Canal, Salivary Apparatus and Digestive Enzymes of Salivary Gland of Catamirus brevipennis (Servile) (Hemiptera: Reduviidae)", (2010) J. entomol. Res. Soc. 12(2):37-50.
Morgan, John Kent, "Developing Molecular Strategies to Control the Asian Cirtus Psyllid, Diaphorina citri (Hemiptera: Liviidae), Vector of Citrus Greening Disease" (Sep. 25, 2013), USDA, PowerPoint Presentation, 11 slides.
Tjallingii, W.F. et al. "Fine structure of aphid stylet routes in plant tissues in correlation with EPG signals", Physiological Entomology, (1993) 18:317-328.
Tjallingii, W. Fred "Salivary secretions by aphids interacting with proteins of phloem wound responses", (2006) Journal of Experimental Botany 57(4):739-745.
Boina, Dhana Raj et al., "Effects of pymetrozine, an antifeedantof Hemiptera, on Asian citrus psyllid, *Diaphorina citri*, feeding behavior, survival and transmission of Candidatus Liberibacter asiaticus", (2010) Pest Management Science 67:146-155.
Walling, Linda L., "Avoiding Effective Defenses: Strategies employed by Phloem-Feeding Insects",(2008) Plant Physiology, 146:859-866.
Wang, Yanchang et al. "Penetration into rice tissues by brown planthopper and fine structure of the salivary sheaths", (2008) Entomologia Experimentalis et Applicata, 129:295-307.
Will, Torsten et al. "Physical and chemical interactions between aphids and plants", (2006) Journal of Experimental Botany 57(4):729-737.
Will, Torsten et al. "Molecular sabotage of plant defense by aphid saliva", (2007) PNAS 104(25):10536-10541.
Will. Torsten et al. "Aphid Gel Saliva: Sheath Structure, Protein Composition and Secretory Dependence on Stylet-tip Milieu" (2012) PLOS One, 7(10):1-8.
Miles, P.W. et al., Evidence that Two Species of Aphid Ingest Food through an Open Stylet Sheath (2010) Experientia XX(10):582.
Moreno, A. et al. "Aphids secrete watery saliva into plant tissues from the onset of stylet penetration" (2011) Entomologia Experimentalis et Applicata 139:145-153.
Harrewijn, Paul et al. Pymetrozine, a Fast-Acting and Selective Inhibitor of Aphid Feeding. In-situ Studies with Electronic Monitoring of Feeding Behaviour (1997), Pestic. Sci. (49)130-140.

\* cited by examiner

METHODS FOR CONTROL OF HEMIPTERAN INSECT STYLET SHEATH STRUCTURE FORMATION

BACKGROUND OF THE INVENTION

Field of the Invention

This invention relates to compositions having at least one compound which inhibits the formation of Hemipteran stylet sheaths, degrades hemipteran style sheaths that have already been formed or deters or blocks hemipteran insects from feeding on plants, especially agriculturally important plants. The invention also relates to methods of using compositions of the present invention to inhibit the formation of hemipteran stylet sheaths, to degrade hemipteran style sheaths that have already been formed, or to deter or block hemipteran insects from feeding on plants, especially agriculturally important plants. This invention also relates to a method of preventing and/or reducing the transmission of vascular associated diseases (caused by hemipteran vector-borne pathogens) to economically important plants.

Description of the Related Art

Insect pests of plants can cause severe plant damage feeding activities initiated to draw nutritional needs from plant tissues. Of these, many plant feeding insects within the Hemiptera order feed by piercing the plant tissues and produce oral secretions that harden into a specialized feeding structure considered essential for insect survival. Many phytophagous hemipterans (true bugs) are characterized by common structural mouthparts (Forero, Revista Colombiana De Entomologia, Volume 34 (1), 1021, 2008) that penetrate host plants inter- or intra-cellularly to feed on contents of vascular tissues or other vegetative cell types. The Order Hemiptera is divided into four clade groups (suborders), the Auchenorrhyncha, Coleorrhyncha, Heteroptera, and Sternorrhyncha (for a systematic review of Hemiptera—see Forero, 2008, (Forero, 2008, supra)). The Sternorrhyncha (Dejean, Gibernau et al., Comptes Rendus De L Academie Des Sciences Seri Ili-Sciences De La Vie-Life Scineces, Volume 323 (5), 447-454, 2000; Howard, Insect On Palms, wallingford, UK; CABI Pub., 2001; Gullan, Encyclopedia of Insects, $2^{nd}$ edn., V. H. Resh, Cardé, R. T., San Diego, Elsevier, 957-967, 2009) including (but not limited to) Psyllidae (e.g. psyllids), Aleyrodidae (e.g. whiteflies), Aphididae (e.g. aphids), Pseudococcidae (e.g. mealybugs), and Coccidae (e.g. scales); the Auchenorrhyncha including (but not limited to) Cicadoidea (e.g. cicadas), Membracoidea (e.g. leafhoppers and treehoppers), Fulgoroidea (e.g. planthoppers), and Cercopoidea (e.g. spittlebugs); and the Heteroptera including (but not limited to) Pentatomidea (e.g. squash bug), contain many agronomically important plant pests that are vectors of pathogens causing plant diseases resulting in vast crop losses worldwide (Backus, Serrano et al., Annual Review of Entomology, Volume 50, 125-151, 2005; Goggin, Current Opinion in Plant Biology, Volume 10(4), 399-408, 2007; Kempema, Cui et al., Plant Physiology, Volume 143(2), 849-865, 2007).

Phytophagous hemipterans feed by penetration of a stylet bundle into plant tissues. A common trait of these insects is the concurrent formation of a solidifying sheath structure, termed stylet sheath that encapsulates the stylet bundle while they penetrate into the plant tissues. As the stylets penetrate various plant tissues, they secrete liquid droplets that solidify to form a solid hollow tube extending from the leaf surface to the point of feeding within the plant tissue, often terminating in the plants vascular tissue (Miles, Advances in Insect Physiology, Volume 9, 183-255, 1972). A subset of these insects also feed more generally on the parenchyma and mesophyll cells of plant tissues, but still produce stylet sheaths as part of the feeding process. Watery and gelling sheath saliva represent two common forms of salivary secretions that are implicated in stylet sheath composition and hemipteran feeding (Miles 1972, supra; Miles, Biological Reviews of the Cambridge Philosophical Society, Volume 74(1), 41-85, 1999; Tjallingii, Journal of Experimental Botany, Volume 57(4), 739-745, 2006; Carolan, Fitzroy et al., Proteomics, Volume 9(9), 2457-2467, 2009; Moreno, Garzo et al., Entomologia Experimentalis Et Applicata, Volume 139(2), 145-153, 2011; Backus, Andrews et al., Journal of Insect Physiology, Volume 58(7), 949-959, 2012; Will, Steckbauer et al., Plos One, Volume 7(10), 2012). The exact function(s) of the stylet sheath in feeding are not known; however, trait conservation across phytophagous hemipterans (Backus, Serrano et al., Annual Review of Entomology, Volume 50, 125-151, 2005), implies biological importance. Stylet sheaths are thought to provide stability and directional orientation to the stylets during the piercing process (Walling, Plant Physiology, Volume 146(3), 859-866, 2008), to aid in proper feeding (Walling 2008, supra), to 'cloak' the stylets from host (plant) defense responses (Miles, 1999, supra), and to rapidly seal cell penetration points during stylet probing (Tjallingii and Esch, Physiological Entomology, Volume 18(3), 317-328, 1993; Will and van Bel, Journal of Experimental Botany, Volume 57(4), 729-737, 2006). This sealing effect is thought to block "plant sensing" of cell damage preventing the perception of increased oxygen and/or rapid changes in pressure, both of which could be signals for induction of plant defenses.

Commonly, stylet sheath initiation occurs concurrently with insect labium contact with host plant surfaces (Miles, Journal of Insect Physiology, Volume 3(3), 243, 1959). Observations indicate that once the insect's labial sensilla encounters a surface (plant or artificial membrane), this surface contact appears to initiate a salivation response from the insect (presumably initiated by sensory mechanisms within the labium) (Miles, Journal of Insect Physiology, Volume 2(4), 338-347, 1958). The secreted saliva that results is presumed to function in assisting the insect to determine the suitability of the surface for feeding. It has been suggested that solidification of sheath material requires interaction with host (plant) components (Lloyd et al., Ohio J. Sci., Volume 87, 50-54, 1987). Additionally, oxygen interactions have been suggested for proper gelling of the flange which is on the leaf surface and the sheath which is found within the leaf tissue (Tjallingii, J. Exp. Bot., Volume 57739-745, 2006; Miles, J. Insect Physiol., Volume 11, 1261-1298, 1965), with a recent report supporting this hypothesis (Will et al., PLoS ONE Volume 7(10), e46903, doi:10.1371/journal.pone.0046903, 2012). Numerous reports using artificial diet systems have allowed the visualization and study of stylet sheaths (Miles, 1999 supra; Miles, J. Insect Physiol., Volume 3, 243-255, 1959; Wang et al., Entomol. Exp. Appl., Volume 129, 295-307, 2008; Cherqui and Tjallingii, J. Insect Physiol., Volume 46, 1177-1186, 2000; Miles, J. Insect Physiol., Volume 4, 2090219, 1960; Miles, J. Insect Physiol, Volume 4, 271-282, 1960; Miles et al., Entomol. Exp. Appl., Volume 59, 123-134, 1991). Stylet sheaths associated with plant tissues begin with a flange (exterior) on the leaf surface, followed (interior) by a narrowing ('neck' region) as the stylet sheath traverses the upper/lower (outer) epidermis of the leaf (Brennan, Weinbaum et al., Biotechnic & Histochemistry, Volume 76(2), 59-66, 2001; Wang, Tang et al., Entomologia Experimentalis, Volume 129(3), 295-307, 2008). This is subsequently followed by a thicker sheath 'shaft' having a continuous sequential bulbous structure as it traverses the tissue to the target region where the sheath may remain as a single channel or branch laterally among the cells of the target tissues (phloem and/or xylem) (Brennan, Weinbaum et al. 2001, supra; Wang, Tang et al. 2008, supra; Lopes, Bonani et al., Entomologia Experimentalis Et Applicata, Volume 134(1), 35-49, 2010). Sheath material has been induced using a brushing technique in sharpshooter (Alhaddad, Coudron et al. Annals of the Entomological Society of America, Volume 103(3), 543-552, 2011); however, the shape of this induced solidified sheath material differs from those formed naturally (Leopold, Freeman et al. Arthropod Structure & Development, Volume 32(2-3), 189-199, 2003; Lopes, Miranda et al. Entomologia Experimentalis Et Applicata, Volume 134(1), 35-49, 2009).

P. W. Miles published a series of papers from the late 1950's to mid 1960's that generally indicate that stylet sheaths are proteinaceous (Miles, 1959, supra; Miles, Journal of Insect Physiology, Volume 4(4), 272-282, 1960; Miles, Journal of Insect Physiology, Volume 10(1), 147-160, 1964; Miles, Kinsey et al. Experientia, Volume 26(6), 611, 1964; Miles, Journal of Insect Physiology, Volume 11(9), 1261-1268, 1965; Miles, Journal of Insect Physiology, Volume 13(12), 1787, 1967); however, Miles' methods indicate that his conclusions may be limited to the flange portion of the insects' secretion (*Oncopeltus fasciatus*, milkweed bug) (Miles, 1959, supra) and not specific to the shaft or branching regions of the stylet sheaths. Subsequently, a host of papers have been published that associate proteins with hemipteran feeding and these indicate multiple proteins are secreted into plants during the probing/feeding processes of various hemipterans (Miles and Harrewijn, Entomologia Experimentalis Et Applicata, Volume 59(2), 123-134, 1991; Madhusudhan and Miles, Entomologia Experimentalis Et Applicata, Volume 86(1), 25-39, 1998; Cherqui and Tjallingii, Journal of Insect Physiology, Volume 46(8), 1177-1186, 2000; Tjallingii, 2006, supra; Will and van Bel, 2006, supra; Will, Tjallingii et al. Proceedings of the National Academy of Sciences of the United States of America, Volume 104(25), 10536-10541, 2007; Carolan, Fitzroy et al. 2009, supra; Cooper, Dillwith et al., Environmenatl Entomology, Volume 39(1), 223-231, 2010; Hattori, Tsuchihara et al., Insect Biochemistry and Molecular Biology, Volume 40(4), 331-338, 2010; Sahayaraj, Kanna et al., Journal of the Entomological Research Society, Volume 12, 37-50, 2010; Alhaddad, Coudron et al. 2011, supra; Backus, Andrews et al., Journal of Insect Physiology, Volume 58(7), 949-959, 2012; Will, Steckbauer et al. 2012, supra). These more recent publications refer to secreted materials that do not appear to have structural implications for stylet sheaths, but rather appear to have a molecular 'effector'-like effects on the host plants (Miles and Sloviak, Experimentia, Volume 26(6), 611, 1970; de Ilarduya, Xie et al., Molecular Plant-Microbe Interactions, Volume 16(8), 699-708, 2003; Tjallingii 2006, supra; Will and van Bel 2006, supra; Will, Tjallingii et al. 2007, supra; Backus, Andrews et al. 2012, supra).

Recently, it was demonstrated that insects will produce stylet sheaths 'in air' (in dere) across a single layer membrane surface (without diet) in 'mock feeding chambers' (MFC) for *Diaphorina citri* (Psyllidae, Asian citrus psyllid), *Aphis nerii* (Aphididae, oleander aphid), *Aphis gossypii* (Aphididae, cotton/melon aphid), *Toxoptera citricida* (Aphididae, brown citrus aphid), *Bemisia tabaci* biotype B (Aleyrodidae, whitefly), *Homalodisca vitripennis* (Cicadellidae, glassy-winged sharpshooter), *Ferrisia virgata* (Pseudococcidae, striped mealybug), and *Protopulvinaria pyriformis* (Coccidae, pyriform scale) (Morgan, et al., PLoS ONE, Volume 8(4), 1-11, Apr. 2013). This membrane probing and stylet sheath formation by these insects is virtually instantaneously induced upon caging and membrane/labium contact with MFC membrane, and they subsequently deposit sheaths that are quite similar in comparison to those formed in plants. For *D. citri* 'feeding' across MFC membranes (membranes typically are either parafilm (common plastic 'kitchen' wrap) or Solvy™ stabilizer membrane (a water-soluble polyvinyl alcohol membrane)), solidification of the stylet sheath occurs rapidly after approximately 45 seconds post-secretion. The solidification process is rapid for stylet sheaths and does not require a lengthy time for solid structures to form. More recently, a technique to isolate intact stylet sheaths utilizing Solvy™ (Sulky of America, Kennisaw, Ga.) and differential filtration (Morgan, et al. 2013 supra).

While there are known methods for controlling hemipteran insects to reduce damage to plants, there is very little known on how to prevent hemipteran insects from feeding on a plant and/or spreading devastating diseases until the present invention. The present invention describes compositions of proteins (such as one or more enzymes and/or lectins) and/or small molecules (such as, but not limited to, metal chelating agents) and/or enzyme inhibitors which reduce or prevent Hemiptera feeding on plants. The present invention also describes methods for using these compositions for controlling Hemiptera damage to plants which is different from the related art methods.

SUMMARY OF THE INVENTION

It is therefore an object of the present invention to provide a composition that inhibits the formation of or solubilizes hemipteran stylet sheaths, disrupts preformed/nascent hemipteran stylet sheaths, and/or prevents or inhibits hemipteran insects from feeding on plants. It is a further object of the present invention is to provide a composition in an effective amount to prevent and/or inhibit the formation of hemipteran stylet sheaths, degrade and/or disrupt preformed/nascent hemipteran stylet sheaths, and thereby reduce or prevent hemipteran insects from feeding on plants and thereby either transmitting the causative agent (pathogen) of a vascular disease to the plant or uptaking the pathogen which causes a vascular disease from the plant. It is another object of this invention to have a method for apply this composition in an effective amount to a plant and to have a kit containing the composition and instructions for use.

It is an object of this invention to have a composition for preventing or reducing hemipteran insect feeding on a plant, the composition containing an agriculturally acceptable carrier, at least one compound effective in preventing or reducing hemipteran insect feeding in an amount effective in preventing formation of said hemipteran insect's stylet sheath or in degrading said hemipteran insect's stylet sheath, and optionally an adjuvant. It is a further object of this invention that the compound can be at least one carbohydrate-degrading enzyme, at least one protease, at least one small molecule that prevents stylet sheath formation, and/or a combination thereof. It is another object of the invention that the protease can be cellulase, protease from *Aspergillus oryzae*, carboxypeptidase, chymopapin, papain, bromelain, ficin, proteinase K, calpain, caspase, cathepsin, actinidin, tobacco etch virus protease, γ-glutamyl hydrolase, and/or a combination thereof. It is another object of the invention that the carbohydrate-degrading enzyme can degrade alpha-(1-4)-glucan polymers and/or beta-(1-4)-glucan polymers. It is another object of this invention that the carbohydrate-degrading enzyme can be, but are not limited to, amyloglucosidase, α-amylase, laminarinase, licheninase, cellulase, hemicellulase, glucuronyl hydrolase, lytic polysaccharide monooxygenase, β-1,4-endoglucanase, endo-1,3(4)-β-glucanases, endodextranase, xylanase, mannan-degrading hydrolase, and/or a combination thereof. It is yet another object of this invention that the small molecule that prevents stylet sheath formation can be 3-aminopropionitrile fumarate salt, dithiothreitol solution, nitrilotriacetic acid trisodium salt, 4-hydroxybenzyl alcohol, kojic acid, ammonium tetrathiomolybdate, ethylenediaminetetraacetic acid (EDTA), D-penicillamine, 2,3,2-tetramine, 2,2,2-tetramine, 1,4,8,11-tetraazacyclotetradecane-1,4,8,11-tetraacetic acid (TETA), N,N',N"-tris(2-pyridylmethyl)-1,3,5-cis,cis,-triaminocyclohexane (tachpyr), naringin, didymin, eriodictyol, eriocitrin, hesperetin, naringenin, 7-hydroxy-coumarin, limonin, limonin glucoside, nomilin, and combinations thereof. It is another object of this invention that the optional adjuvant can be at least one buffer, a penetrating agent, at least one surfactant, at least one oil, at least one humectant, or a combination thereof. It is another object of this invention to have a method for apply this composition in an effective amount to a plant and to have a kit containing the composition and instructions for use.

It is an object of this invention to have a composition for preventing or reducing hemipteran insect feeding on a plant, the composition containing an agriculturally acceptable carrier, at least one compound effective in preventing or reducing hemipteran insect feeding in an amount effective in preventing formation of said hemipteran insect's stylet sheath or in degrading said hemipteran insect's stylet sheath, and optionally an adjuvant. It is a further object of this invention that the compound can be at least one carbohydrate-degrading enzyme, at least one protease, at least one small molecule that prevents stylet sheath formation, and/or a combination thereof. It is another object of this invention that the small molecule is a metal chelating agent that inhibits laccase. It is further object of this invention that the small molecule is a copper chelating agent or other type of laccase inhibitor. It is another object of this invention that the optional adjuvant can be at least one buffer, a penetrating agent, at least one surfactant, at least one oil, at least one humectant, or a combination thereof. It is another object of this invention to have a method for apply this composition in an effective amount to a plant and to have a kit containing the composition and instructions for use.

A still further object of the present invention is to provide a composition in an amount effective to solubilize or inhibit the formation of hemipteran stylet sheaths, disrupt preformed/nascent hemipteran stylet sheaths, and/or deter or block hemipteran insects from feeding on plants, having at least one carbohydrate-degrading enzyme that degrades alpha-(1-4)-glucan polymers. It is another object of this invention that the composition can optionally include an adjuvant where the adjuvant can be at least one buffer, at least one penetrating agent, at least one surfactant, at least one oil, at least one humectant, and a combination thereof. It is another object of this invention to have a method for apply this composition in an effective amount to a plant and to have a kit containing the composition and instructions for use.

A still further object of the present invention is to provide a composition in an amount effective to solubilize or inhibit the formation of hemipteran stylet sheaths, disrupt preformed/nascent hemipteran stylet sheaths, and/or deter or block hemipteran insects from feeding on plants, having at least one carbohydrate-degrading enzyme degrades beta-(1-4)-glucan polymers. It is another object of this invention that the composition can optionally include an adjuvant where the adjuvant can be at least one buffer, at least one penetrating agent, at least one surfactant, at least one oil, at least one humectant, and a combination thereof. It is another object of this invention to have a method for apply this composition in an effective amount to a plant and to have a kit containing the composition and instructions for use.

A still further object of the present invention is to provide a composition in an amount effective to solubilize or inhibit the formation of hemipteran stylet sheaths, disrupt preformed/nascent hemipteran stylet sheath, and/or deter or block hemipteran insects from feeding on plants, having at least one protease, such as, but not limited to, *Aspergillus oryzae* protease, carboxypeptidase W from wheat, chymopapain from papaya latex, papain from papaya latex, bromelain from pineapple stem, ficin from fig tree latex, and mixtures thereof. It is another object of this invention that the composition can optionally include an adjuvant where the adjuvant can be at least one buffer, at least one penetrating agent, at least one surfactant, at least one oil, at least one humectant, and a combination thereof. It is another object of this invention to have a method for apply this composition in an effective amount to a plant and to have a kit containing the composition and instructions for use.

Another aspect of the present invention is to provide a composition in an effective amount to solubilize or inhibit the formation of hemipteran stylet sheaths, disrupt preformed/nascent hemipteran stylet sheath, and/or deter or block hemipteran insects from feeding on plants, the composition containing at least one small molecule that inhibits the polymerization process of the stylet sheath formation, or disrupts the formation of or already formed stylet sheath via an unknown mechanism. A further object of this invention is that the at least one small molecule can be a metal chelating compound, and more particularly, a copper chelating compound. Another object of this invention is that the small molecule can be a laccase inhibitor. A further object of this invention is that the small molecule can be 3-aminopropionitrile fumarate salt, dithiothreitol solution, nitrilotriacetic acid trisodium salt, 4-hydroxybenzyl alcohol, kojic acid, ammonium tetrathiomolybdate, ethylenediaminetetraacetic acid (EDTA), D-penicillamine, 2,3,2-tetramine, 2,2,2-tetramine, 1,4,8,11-tetraazacyclotetradecane-1,4,8,11-tetraacetic acid (TETA), N,N',N"-tris(2-pyridylmethyl)-1,3,5-cis,cis,-triaminocyclohexane (tachpyr), naringin, didymin, eriodictyol, eriocitrin, hesperetin, naringenin, 7-hydroxy-coumarin, limonin, limonin glucoside, nomilin, and/or a combination thereof. It is another object of this invention that the composition can optionally include an adjuvant where the adjuvant can be at least one buffer, at least one penetrating agent, at least one surfactant, at least one oil, at least one humectant, and a combination thereof. It is another object of this invention to have a method for apply this composition in an effective amount to a plant and to have a kit containing the composition and instructions for use.

It is another object of this invention to provide a method for preventing the polymerization process of stylet sheath formation that includes applying to a plant a composition that prevents polymerization of the stylet sheath in an amount effective to inhibit stylet sheath polymerization, where the composition contains a small molecule, an agriculturally acceptable carrier, and optionally an adjuvant. It is another object of this invention that the small molecule can be a metal chelating compound, such as a copper chelating compound. It is another object of this invention that the small molecule can be a laccase inhibitor. It is a further object of this invention that the small molecule can be 3-aminopropionitrile fumarate salt, dithiothreitol solution, nitrilotriacetic acid trisodium salt, 4-hydroxybenzyl alcohol, kojic acid, ammonium tetrathiomolybdate, ethylenediaminetetraacetic acid (EDTA), D-penicillamine, 2,3,2-tetramine, 2,2,2-tetramine, 1,4,8,11-tetraazacyclotetradecane-1,4,8,11-tetraacetic acid (TETA), N,N',N''-tris(2-pyridylmethyl)-1,3,5-cis,cis,-triaminocyclohexane (tachpyr), naringin, didymin, eriodictyol, eriocitrin, hesperetin, naringenin, 7-hydroxy-coumarin, limonin, limonin glucoside, nomilin, and/or a combination thereof. It is a further object of the invention that the optional adjuvant can be at least one buffer, at least one penetrating agent, at least one surfactant, at least one oil, at least one humectant, and/or a combination thereof.

Another object of the present invention is to provide a method for prevention or blocking hemipteran insects from feeding on plants or reducing the feeding of hemipteran insects on plants by applying to a plant an effective amount of a composition to prevent or block hemipteran insects from feeding or to reduce hemipteran insect feeding on the plant; the composition containing at least one carbohydrate-degrading enzyme or at least one protease, or mixtures thereof. It is a further object of this invention that the composition contain an agriculturally acceptable carrier and optionally an adjuvant which can be at least one buffer, at least one penetrating agent, at least one surfactant, at least one oil, at least one humectant, and/or a combination thereof. It is yet another object of this invention that the protease can be cellulase, protease from *Aspergillus oryzae*, carboxypeptidase, chymopapin, papain, bromelain, ficin, proteinase K, calpain, caspase, cathepsin, actinidin, tobacco etch virus protease, γ-glutamyl hydrolase, and/or a combination thereof; and the carbohydrate-degrading enzyme can be amyloglucosidase, α-amylase, laminarinase, licheninase, cellulase, hemicellulase, glucuronyl hydrolase, lytic polysaccharide monooxygenase, β-1,4-endoglucanase, endo-1,3 (4)-β-glucanases, endodextranase, xylanase, mannan-degrading hydrolase, and/or a combination thereof. It is a further object of this invention that the composition can include at least one small molecule, such as 3-aminopropionitrile fumarate salt, dithiothreitol solution, nitrilotriacetic acid trisodium salt, 4-hydroxybenzyl alcohol, kojic acid, ammonium tetrathiomolybdate, ethylenediaminetetraacetic acid (EDTA), D-penicillamine, 2,3,2-tetramine, 2,2,2-tetramine, 1,4,8,11-tetraazacyclotetradecane-1,4,8,11-tetraacetic acid (TETA), N,N',N''-tris(2-pyridylmethyl)-1,3,5-cis,cis,-triaminocyclohexane (tachpyr), naringin, didymin, eriodictyol, eriocitrin, hesperetin, naringenin, 7-hydroxy-coumarin, limonin, limonin glucoside, nomilin, and/or a combination thereof. It is yet another object of this invention that by reducing or preventing hemipteran feeding on a plant, the transmission (between the hemipteran insect and the plant) of a pathogen that causes vascular disease in a plant can be reduced or prevented.

Further objects and advantages of the present invention will become apparent from the following description.

BRIEF DESCRIPTION OF THE DRAWINGS

FIG. 2E, are compared to various glucose polymers (cellobiose, micro-granular cellulose, dextrin, corn starch, and dextrin, respectively). Regions of interest corresponding to either the O—H bond or the C—O single bond regions are approximately 3200-3600 $cm^{-1}$, and approximately 1150-950 $cm^{-1}$, respectively.

FIGS. 3A-3C and 3D-3F are micrographs of the same ACP SSs (respectively) viewed out the experiment. FIGS. 3A and 3D are time zero (T0) cellulase treatment while FIGS. 3B and 3E are at 72 hours post-cellulase treatment. FIGS. 3C and 3F are micrographs of sheaths from 3B and 3E, respectively, after application of gentle pressure on the glass cover-slip that was placed over the sheaths. Fracture of the sheaths is clearly visible indicating loss of integrity because of the cellulase treatment. Subsequent studies have shown that no more than about 30 minutes is required to obtain the plump conformation of the stylet sheaths (see FIGS. 3B and 3E). FIGS. 3G, 3H, and 3I show the lack of stylet sheath formation in the presence of the cellulase enzyme in the diet.

FIG. 4A is a light micrograph of a fully formed *D. citri* salivary sheath structure isolated from a water dissolvable membrane (Solvy™) with both flange and sheath attached. FIGS. 4D, 4E, 4F, 4G, 4H, and 4I are light micrographs of sites where *D. citri* fed on liquid diets containing either: 3-aminopropionitrile fumarate salt (also known as β-aminopropionitrile or BAPN) (a lysyl oxidase inhibitor) (FIG. 4D), or different proteases with varying modes of action: carboxypeptidase W (FIG. 4E), chymopapain (FIG. 4F), bromelain (FIG. 4G), papain (FIG.

Figure 4A:
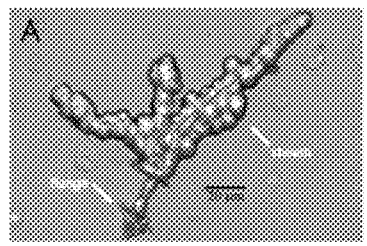
FIGS. 4A 4I are micrographs of ACP SSs treated with enzyme inhibitors that block sheath formation or proteases that block sheath formation and/or degrade already synthesized sheaths.
Figure 4B:
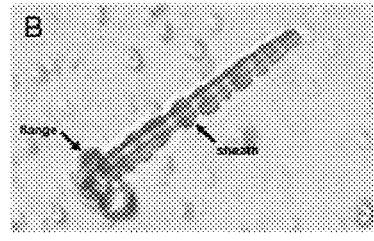
FIG. 4B is a light micrograph of a *D. citri* salivary sheath formed across a membrane in 1× artificial diet (sheath stained green from diet).
Figure 4C:
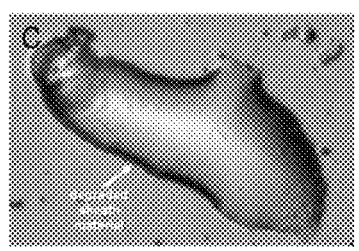
FIG. 4C is a *D. citri* salivary sheath treated with Flavourzyme (protease cocktail) for about 30 minutes that indicates digestion of a previously solidified salivary sheath.
Figure 4D:
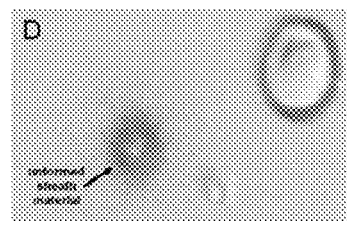
Figure 4E:
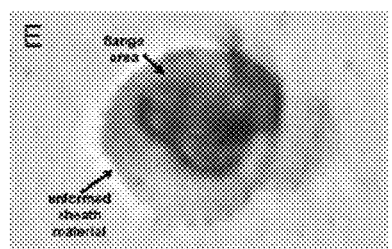
Figure 4F:
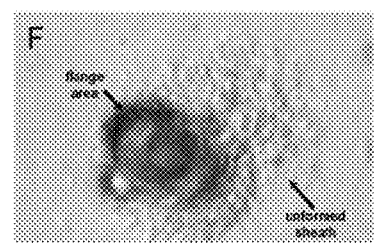
Figure 4G:
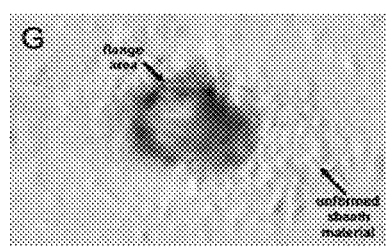
Figure 4H:
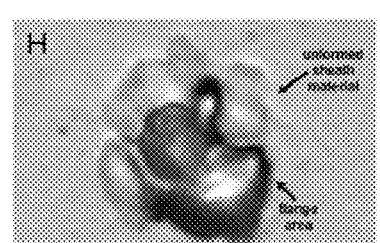
Figure 4I:
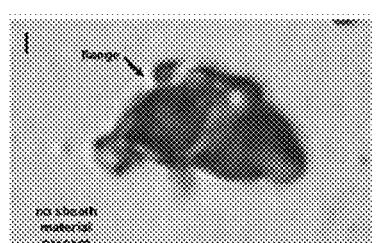

4H), and ficin (FIG. 4I), indicating either the prevention of solid sheath formation based on presence of material that appears to be un-solidified sheath debris (FIGS. 4D 4H), or the abortion of *D. citri* feeding attempts where no sheath debris is visible (FIG. 4I).

Figure 5A:
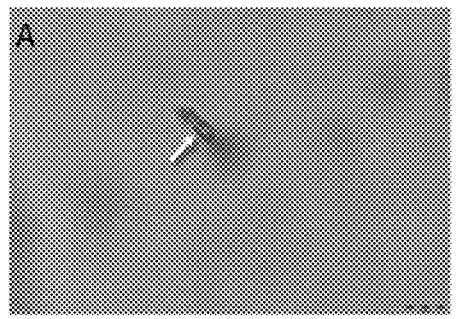
Figure 5B:
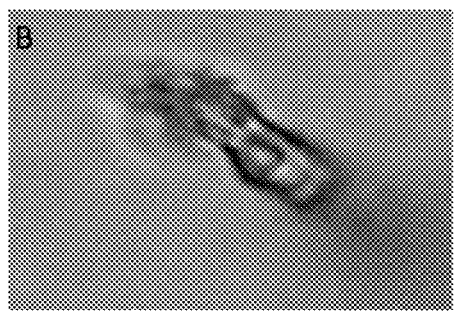
Figure 5C:
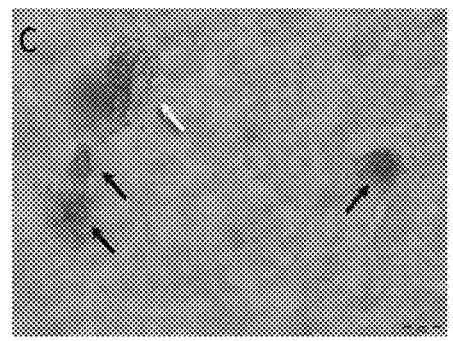
Figure 5D:
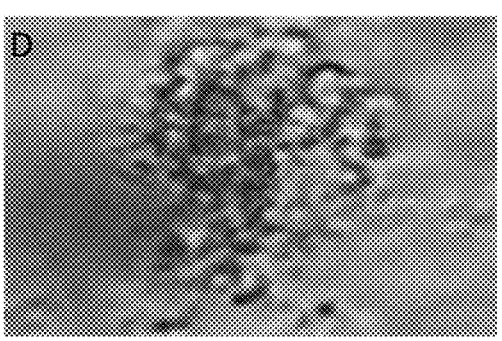
Figure 5E:
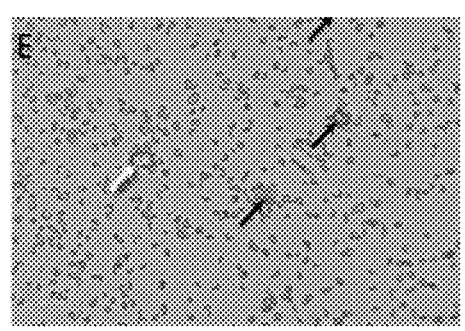
Figure 5F:
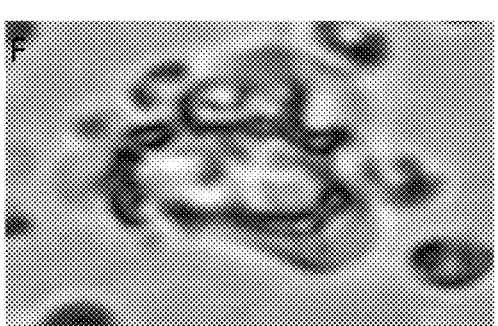

FIGS. 5A-5F are micrographs of whitefly stylet sheaths formed in whitefly diet either with or without the presence of specific proteases in the diet. FIG. 5A and FIG. 5B (enlargement of FIG. 5A at arrow) show the control which is a whitefly sheath in a diet free of bromelain and ficin. FIGS. 5C 5F show effect on sheath formation of diets containing either 10 units/mL bromelain (FIG. 5C and FIG. 5D (enlargement of FIG. 5C at white arrow)) or 10 units/mL ficin (FIG. 5E and FIG. 5F (enlargement of FIG. 5E at white arrow) proteases showing the inhibition of stylet sheath formation and/or the deterrence of whitefly feeding events. In FIG. 5C, black and white arrows indicate attempted stylet sheath forming events that were each inhibited by the presence of bromelain protease. FIG. 5D shows an attempted feeding event where the secreted stylet sheath material did not form a solid sheath structure, but was randomly dispersed into the diet in the presence of bromelain in the diet. In FIG. 5E black and white arrows show attempted whitefly-feeding events that were aborted by the whiteflies because of the presence of ficin. All images are 600×.

Figure 6A:
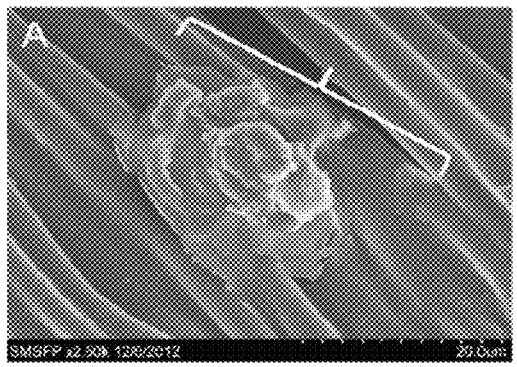
Figure 6B:
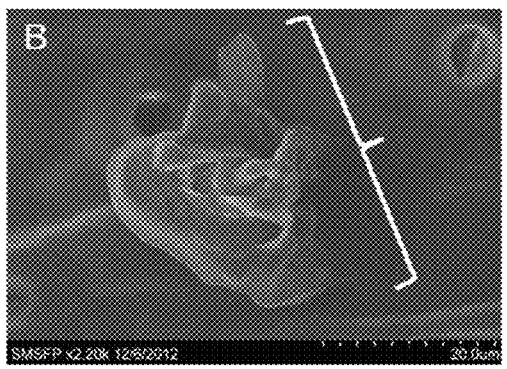
Figure 6C:
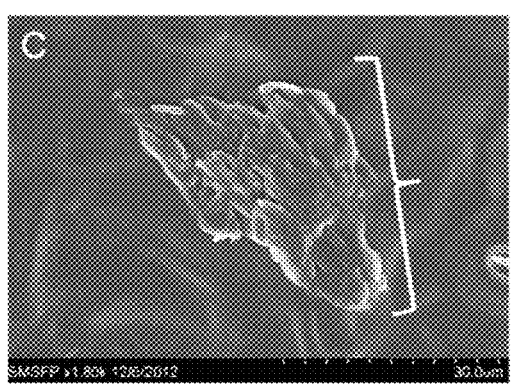
Figure 6D:
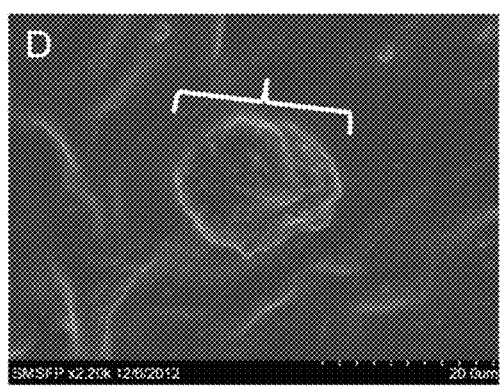
Figure 6E:
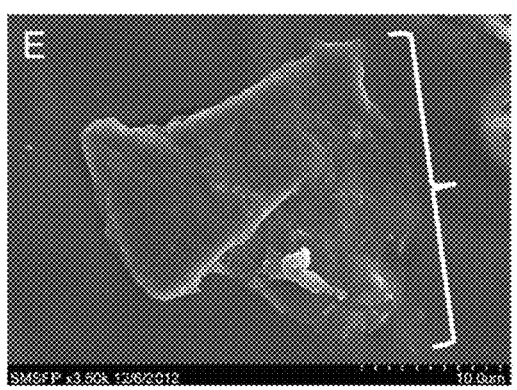
Figure 6F:
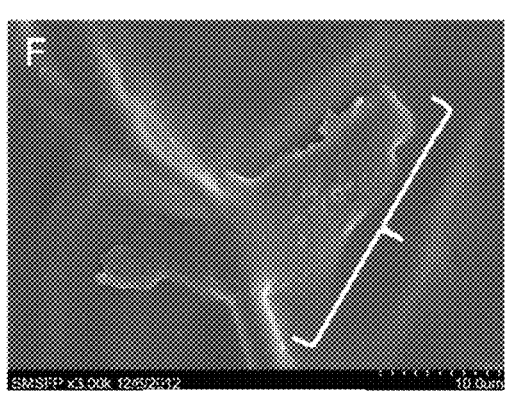

FIGS. 6A 6F are micrographs showing the effects of proteases applied to *Citrus macrophylla* leaf surfaces on *Diaphorina citri* (psyllid) stylet sheath formation while the psyllid feeds. The treatments included ficin at 1 unit/ml, combination of ficin and bromelain at 1 unit/ml, and HEPES buffer as a control. FIGS. 6A and 6B are scanning electron micrograph images (SEM) of HEPES treated control *C. macrophylla* leaf surfaces that show normal stylet flange formation deposits (highlighted by brackets) indicating normal feeding attempts occurred. FIGS. 6C and 6D are SEM images of ficin treated *C. macrophylla* leaf surfaces having 'non-typical' stylet sheath flange formation (see bracketed areas). FIGS. 6E and 6F are SEM images of combination of ficin and bromelain treated *C. macrophylla* leaf surfaces indicating 'highly-deformed' stylet sheaths (see bracketed areas).

Figure 7A:
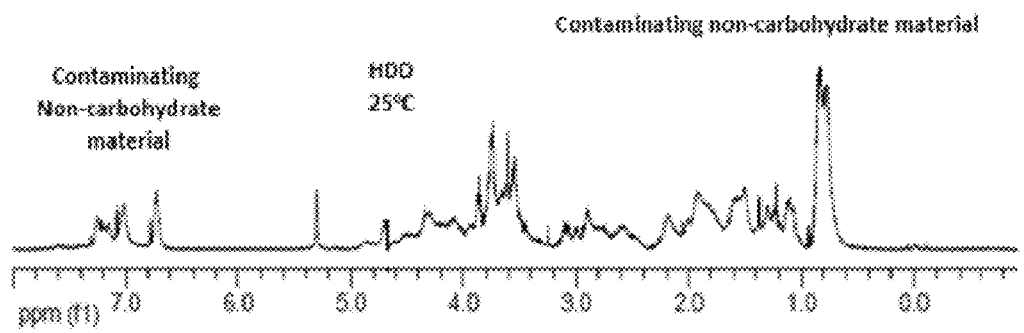
Figure 7B:
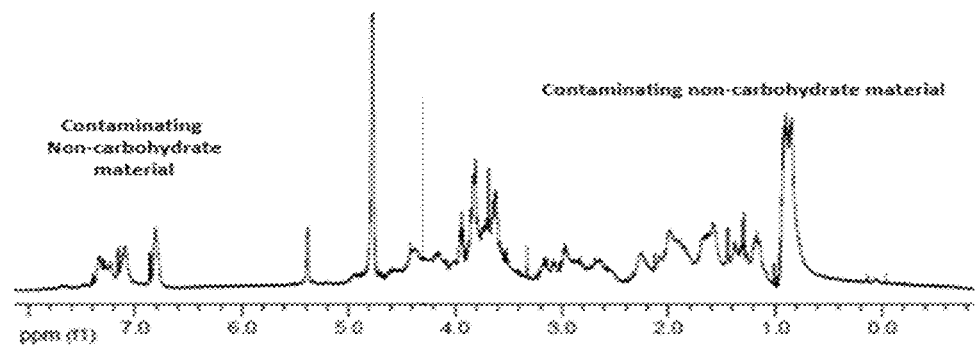
Figure 7C:
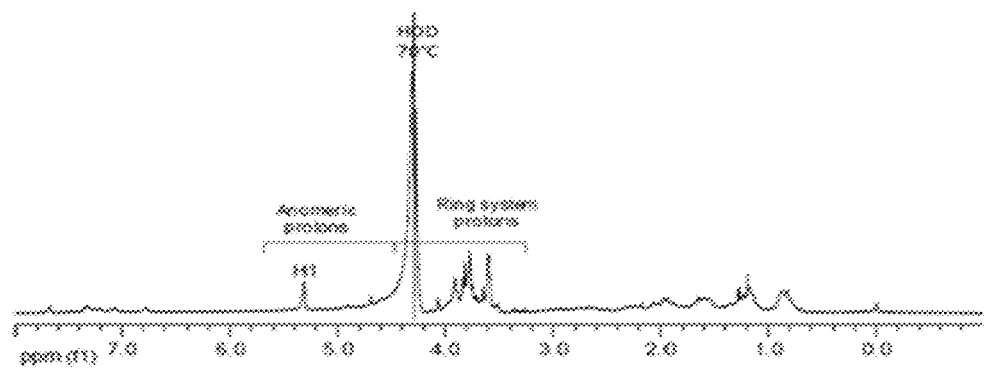

FIGS. 7A-7C illustrate a comparative chemical analysis by proton nuclear magnetic resonance (NMR) of proteinase K treated verses non-proteinase K treated ACP SS. FIG. 7A is the NMR spectrum of non-proteinase K treated ACP SS. FIG. 7B is the NMR spectrum of ACP SS after treatment with proteinase K. FIG. 7C is the NMR spectrum of ACP SS that were treated with proteinase K. For FIGS. 7A, 7B, and 7C, after proteinase K treatment, the sample is dialyzed using a 1,000 molecular weight cut off (MWC) bag, and then analyzed by proton NMR. The spectra for FIGS. 7A and 7B are acquired at 25° C., while FIG. 7C is acquired at 70° C.

Figure 8:
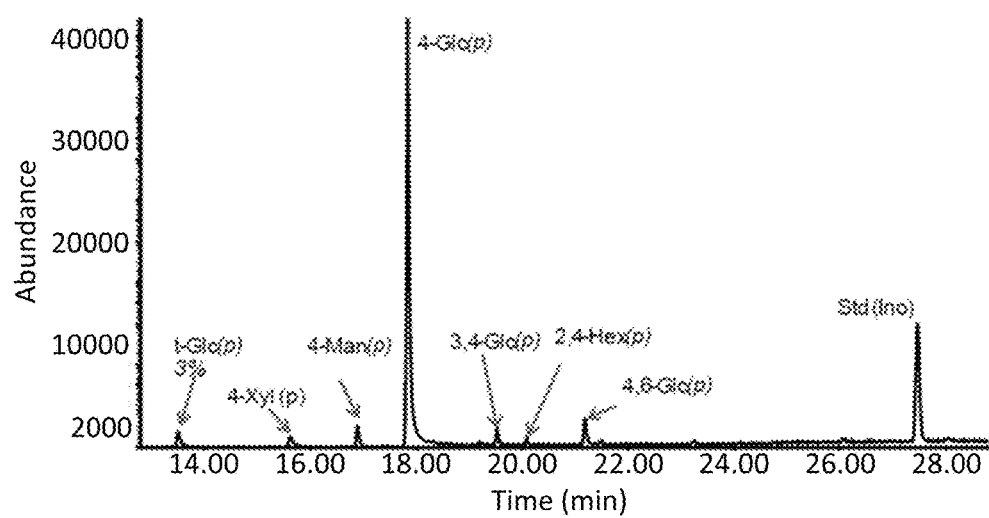

FIG. 8 is a gas chromatography mass spectrum (GC-MS) spectra of partially methylated alditol acetates (PMAA) treatment of proteinase K treated and dialyzed (1,000 MWC) ACP SS material. The y-axis indicates the hydrolyzed sugars associated with ACP SS indicating the presence of glucose (Glc), xylose (Xyl), mannose (Man), and hexose (Hex) in their pyranose (p) form. The numerical prefix indicates sites on the carbon ring where methylation occurred during the PMAA process. For example in the case of 4-Glc(p), it was methylated at carbon #4 during the PMAA process and all other carbons in the 4-Glc(p) were occupied by other bonding that prevented methylation at the other carbon sites in the ring. These finding indicate the probability that the ACP SS are highly branched polysaccharides and that 4-Glc (p) is the most abundant sugar in the ACP SS structure.

Figure 9A:
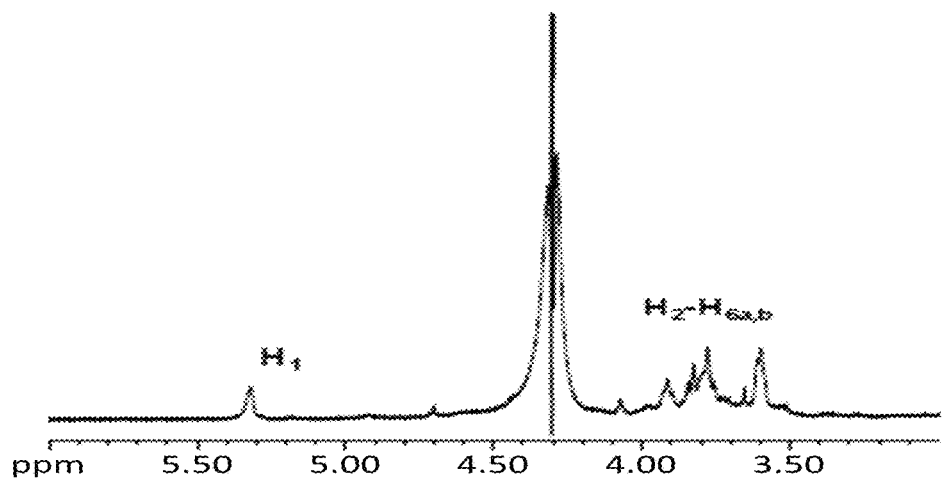
Figure 9B:
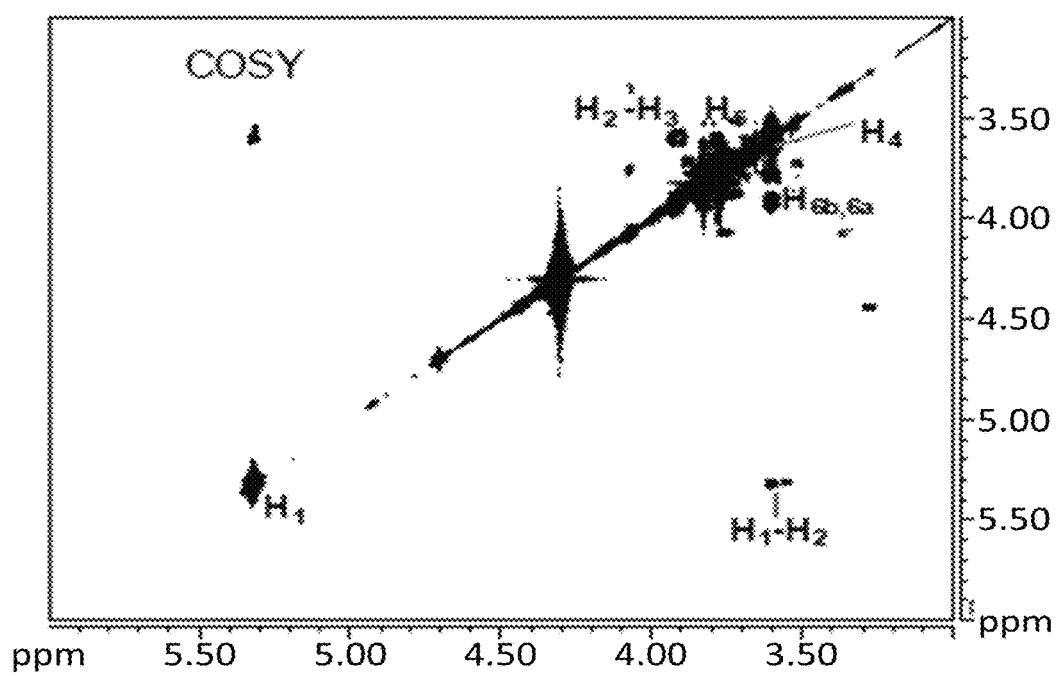
Figure 9C:
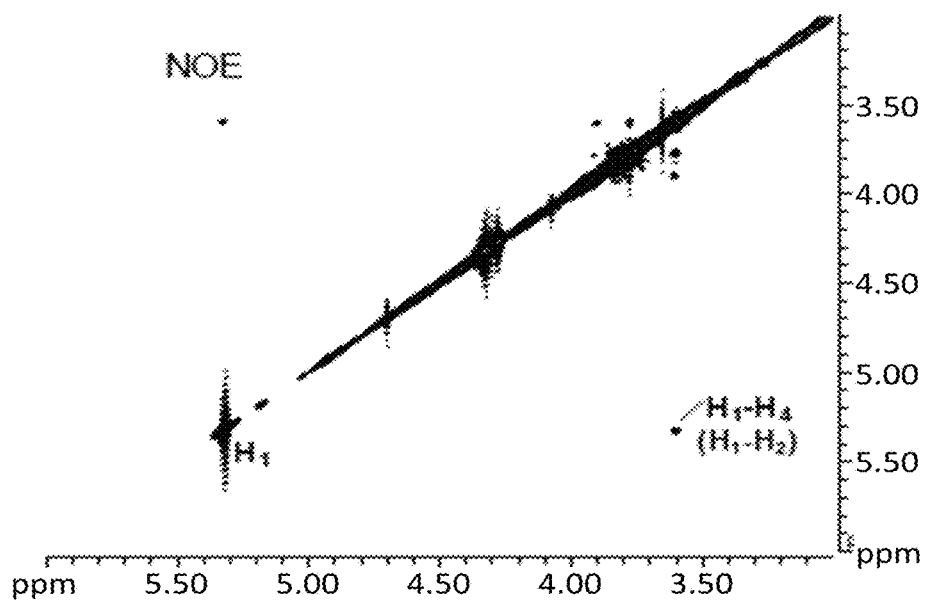
Figure 9D:
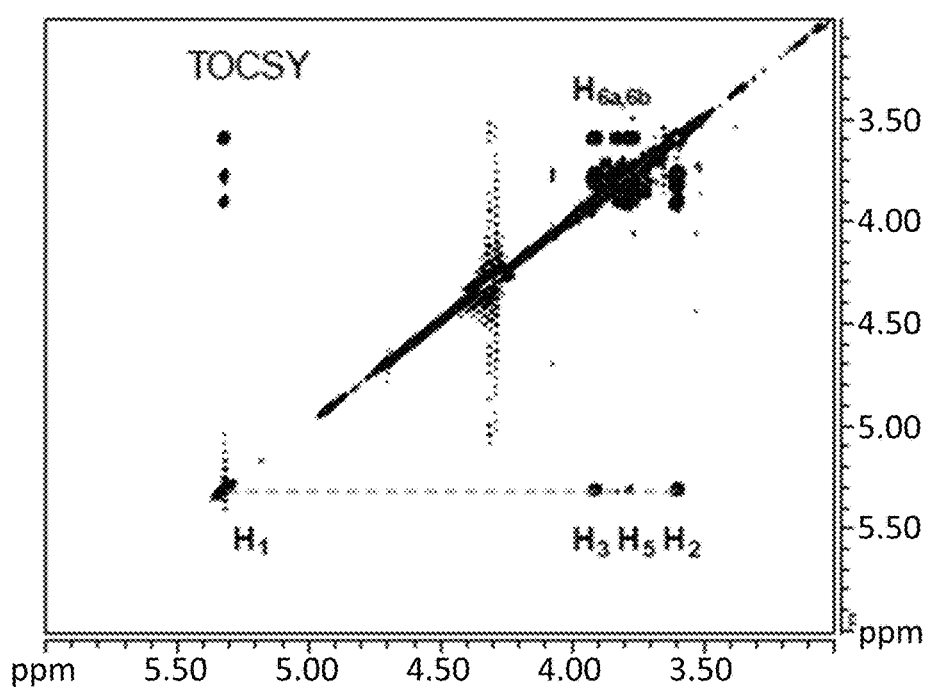
Figure 9E:
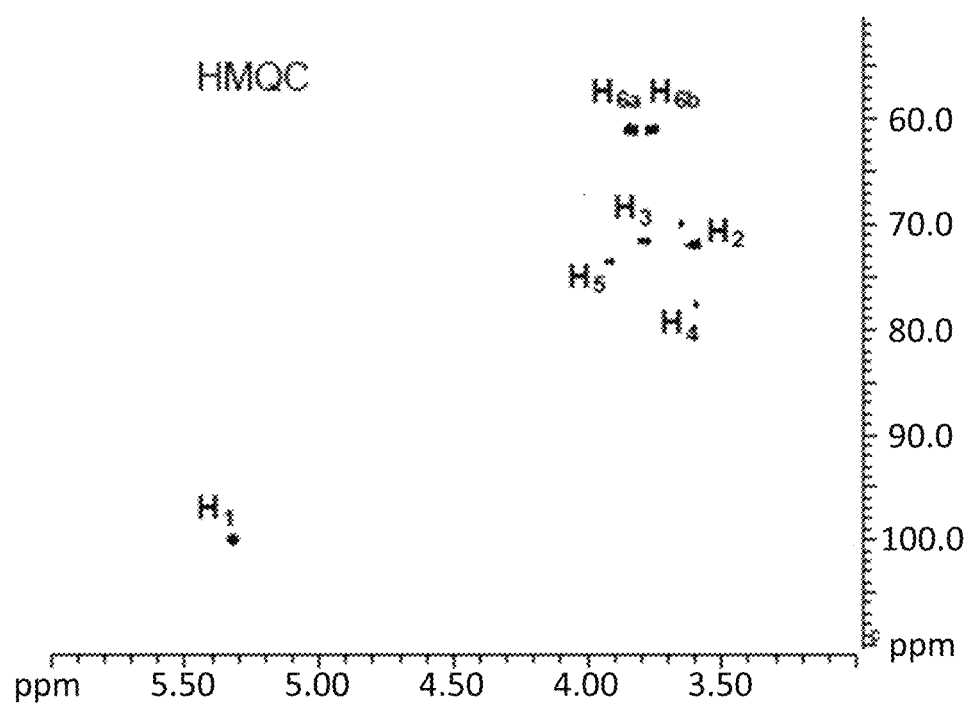

FIGS. 9A 9E are multi-dimensional (1D and 2D) spectra of proteinase K treated and dialyzed (1,000 molecular weight cut off) ACP SS by nuclear magnetic resonance (NMR). FIG. 9A is a 1D-Presat spectrum. FIGS. 9B-9E are 2D spectra of Correlation spectroscopy (COSY), Nuclear Overhouser Effect (NOE), Total Correlation Spectroscopy (TOCSY), and Heteronuclear multiple-quantum correlation spectroscopy (HMQC), respectively. All spectra were recorded at 70° C. and calibrated to internal standard of tetramethylsilane (TMS). For orientation, anomeric hydrogen (H1) signals for alpha-sugars resonate at 4.8-5.3 parts per million (ppm); whereas, beta-sugars resonate at 4.4-4.8 ppm. These data indicate the presence of both alpha and beta bonding in the ACP SS structure as indicated by the peaks at 5.3 ppm (alpha) and 4.7 ppm (beta) in FIGS. 9A 9D. The 2D HMQC analysis (FIG. 9E) illustrates the correlation of carbons and bonded hydrogens. The x-axis is hydrogen (H) and the y-axis is carbon (C) in ppm, respectively.

Figure 10A:
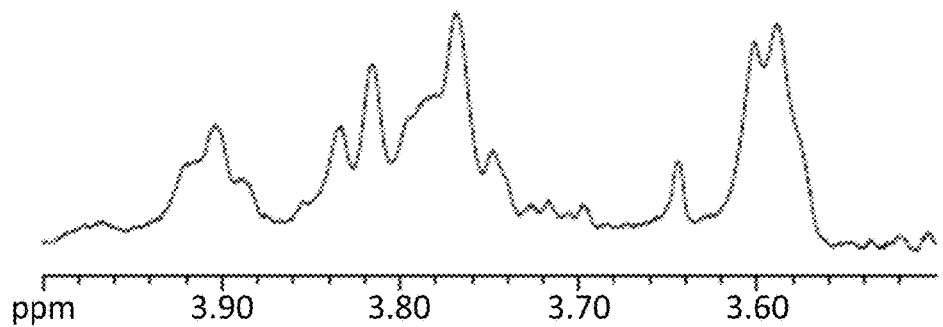
Figure 10B:
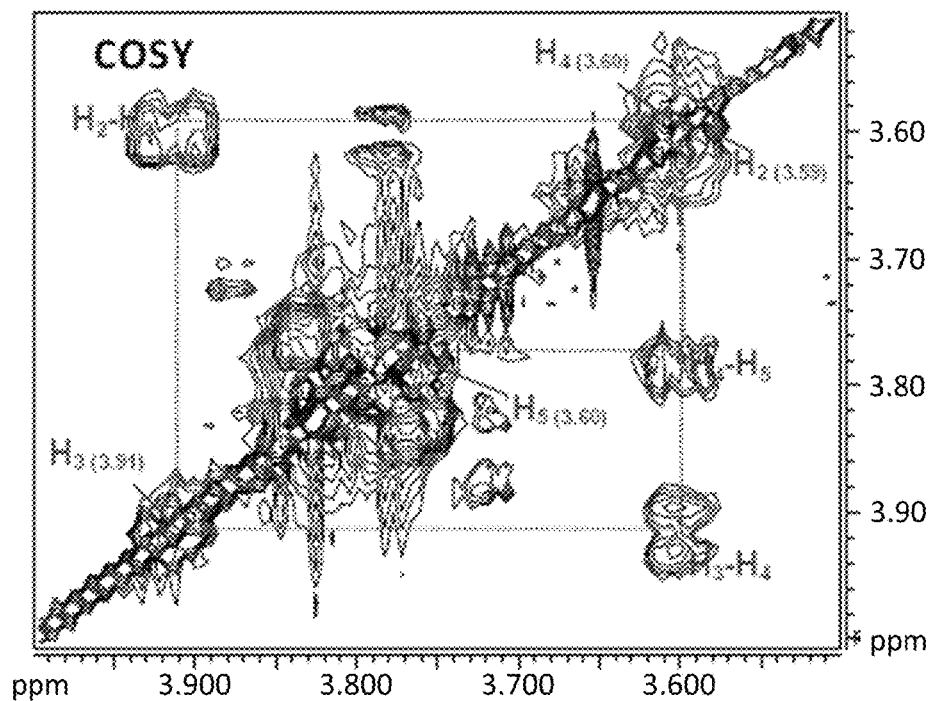
Figure 10C:
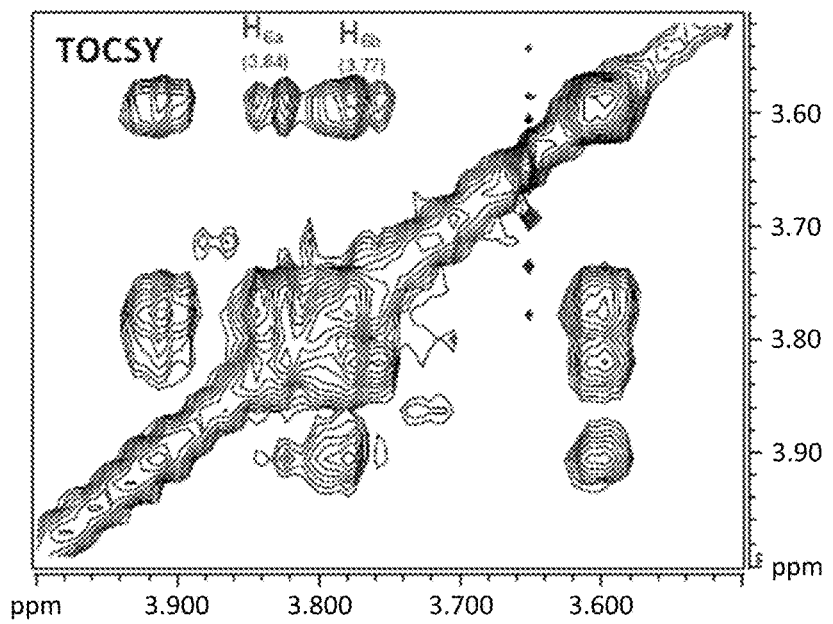
Figure 10D:
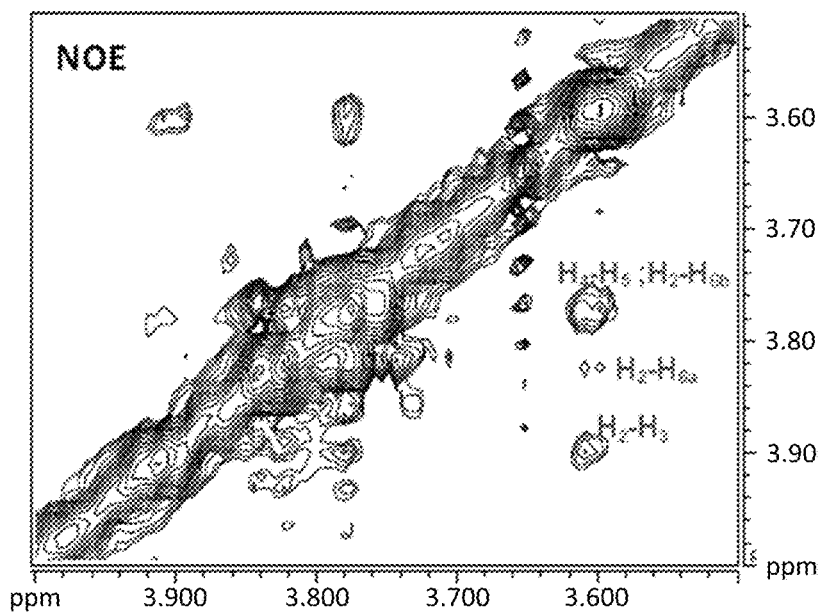
Figure 10E:
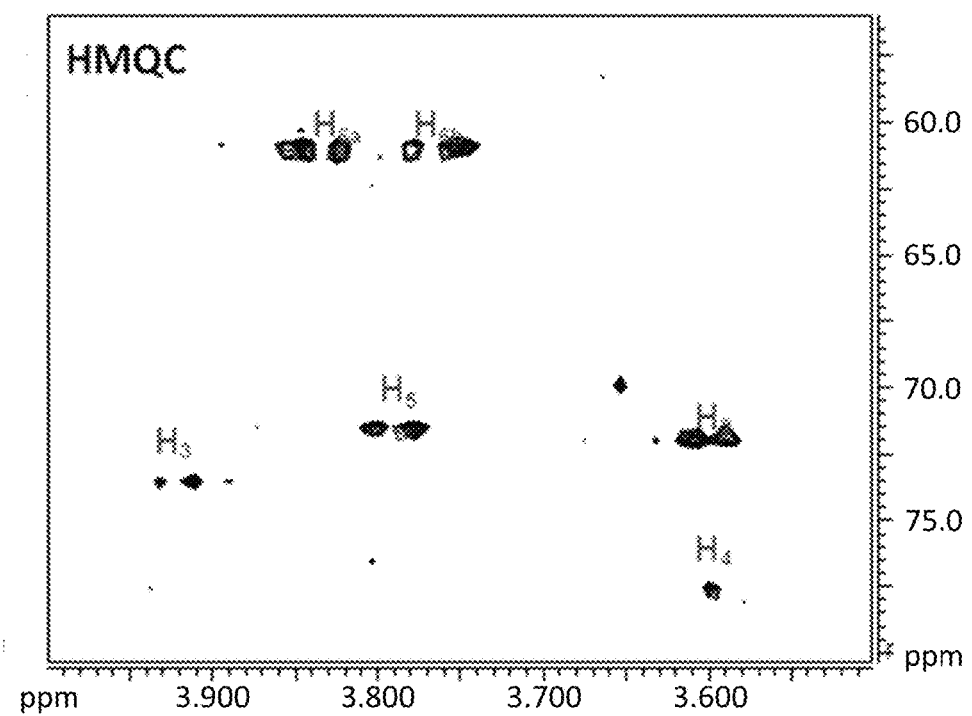

FIGS. 10A 10E are expansion views of the spectra from FIGS. 9A 9E from the 3.5-4.0 ppm range for hydrogen resonance.

Figure 11A:
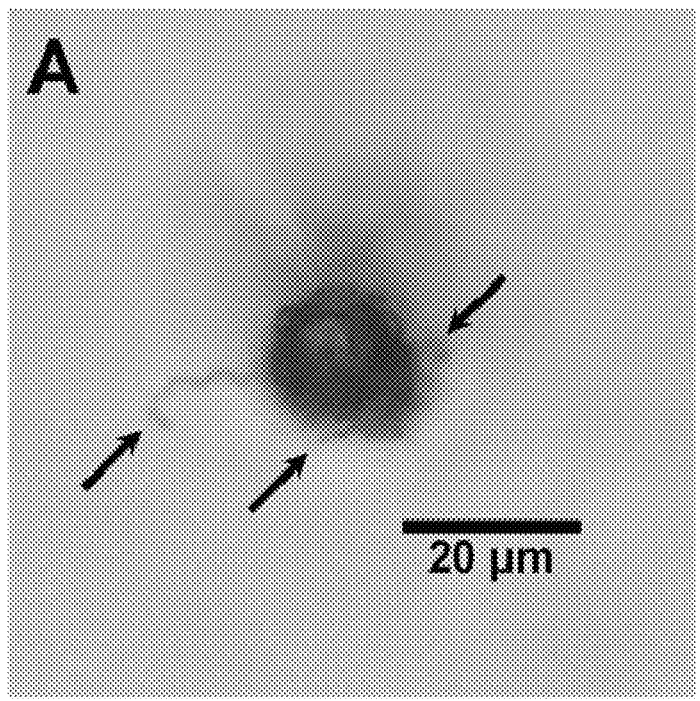
Figure 11B:
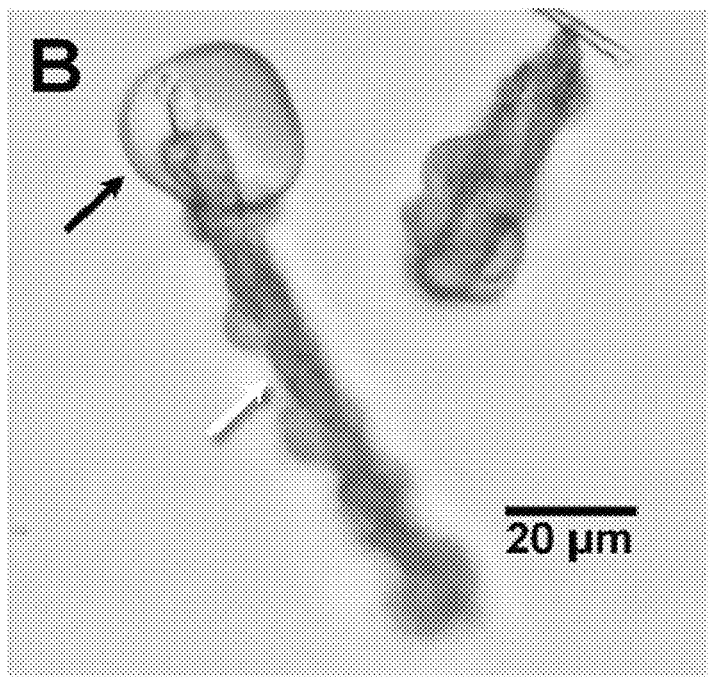

FIG. 11A shows a malformed ACP stylet sheath that was formed in an artificial diet containing eriocitrin. Black arrows indicate where abnormal 'side projections' of stylet sheath material are formed. FIG. 11B shows inhibition of flange solidification of the ACP stylet sheath when fed an artificial diet containing nomilin (black arrow) yet the production of a normal shaft (white arrow).

DETAILED DESCRIPTION OF THE INVENTION

There is a need for novel compositions and methods which prevent hemipteran insects from damaging economically important plants and/or reduce the amount of damage hemipteran insects cause on economically important plants. These compositions and methods can either inhibit or reduce the feeding of hemipteran insects on economically important plants. One embodiment of this control strategy is that insect feeding is blocked before the insect can reach the plant vascular tissue with its probing mouth parts. This blocking could be realized by presence of either sheath formation inhibitors or sheath degrading molecules on the surface of the leaf and/or present within the intercellular spaces of the different leaf tissues. This embodiment differs from the delivery strategy of systemic chemical pesticides which move systemically in the plant the vascular tissue and from pesticides that allow feeding to proceed prior to the insect's death at some time after pesticide acquisition by the insect. Preventing and/or reducing insect feeding can have a great economic importance for many insect vectored diseases, especially those diseases that are limited to the vascular tissues of the plant. If the insect cannot reach the plant vascular tissue with its probing mouth parts, it can neither acquire nor transmit these pathogens. As an example, transmission of citrus greening disease associated with the phloem limited bacterial species of the '*Candidatus*' Liberibacter genus is still an economic issue in citrus treated with systemic neonicotinoid pesticides because the insects will still feed for a brief period of time before succumbing to the insecticide and therefore will still transmit the bacterium (Gatinearu et al., *Fruits* 65:4 209-220 (2010)). Thus, this invention also involves preventing and/or reducing the transmission of vascular associated diseases (caused by hemipteran vector-borne pathogens) to economically important plants.

Using the methods described in Morgan et al. 2013, supra, it is possible to obtain Hempitera stylet sheaths and determine the composition of the stylet sheaths. Because pure sheaths can be isolated in this manner, it has been possible to determine sheath compositions. Composition information can be used to rationally identify molecules that inhibit stylet sheath formation, reduce the quantity and/or quality of the stylet sheaths, and/or degrade previously formed stylet sheaths. By reducing or inhibiting the amount and/or the quality of feeding, and/or degrading already formed stylet sheaths, one can reduce or prevent transmission of vascular associated diseases from Hempitera to economically important plants. Further, one can also prevent or reduce damage to economically important plants caused by Hempitera that feed on such plants.

The MFCs are an adaptable platform to allow for new observational methods by SEM and light microscopy to obtain both high resolution still and video images of form and formation of stylet sheaths for Hemiptera insects. Stereomicroscopy and inverted light microscopy of MFC chambers provide both still and video imagery of stylet sheath formation without solid or liquid diet obstruction.

Figure 1A:
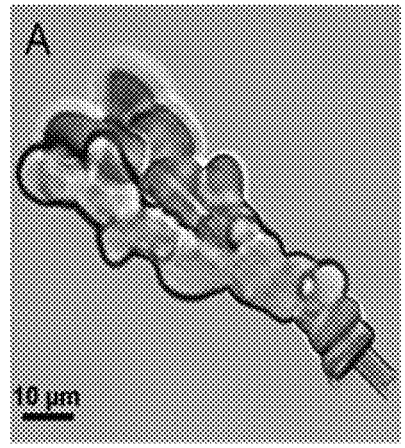
FIG. 1A is a light micrograph of a *D. citri* stylet sheath (SS). It contains a portion of the sheath that would be near the flange portion of the SS (a section of the SS that is formed on the surface of the leaf) and a shaft (the portion of the sheath that is polymerized in the leaf tissue after the insect mouthparts have penetrated the leaf surface).
Figure 1B:
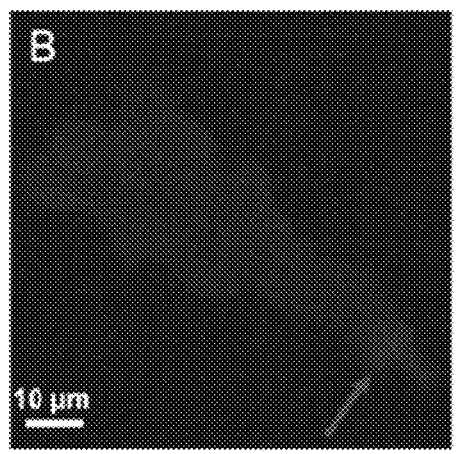
FIG. 1B is a confocal laser excited micrograph of the same *D. citri* stylet sheath as viewed in FIG. 1A that shows the area near the flange area portion (see grey arrow) exhibits greater intensity of auto-fluorescence relative to the shaft when excited by a confocal laser beam.
Figure 1C:
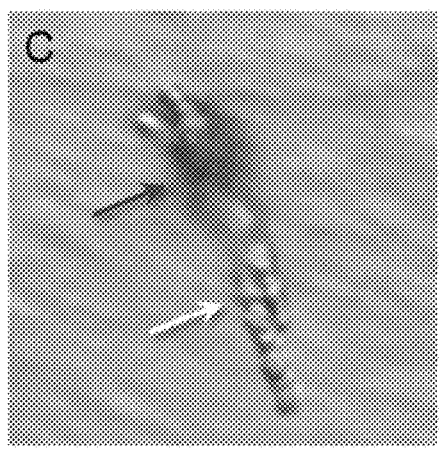
FIG. 1C is a light micrograph of a *D. citri* stylet sheath (different from the one in FIG. 1A).
Figure 1D:
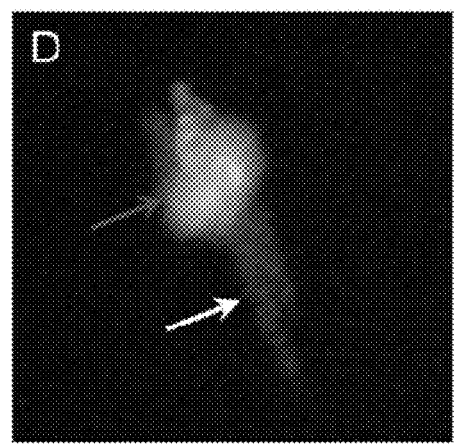
FIG. 1D is an UV excited micrograph of the *D. citri* stylet sheath of FIG. 1C showing that the shaft (grey arrow) exhibits greater intensity of auto-fluorescence relative to the flange (white arrow) corroborating what is seen in FIG. 1B where the SS portion proximal to the flange is more highly autofluorescent. This difference in fluorescence intensity is indicative of different composition and/or bond structure between the molecular components of the shaft and the flange.

As described more fully in the examples, infra, the composition of stylet sheaths vary between the flange and stylet shaft/branching portions. Using auto-fluorescence, differences in the relative intensity of fluorescence between the flange and shaft/branching portions of the stylet sheaths can be visualized (see FIGS. 1A and 1B). Also, differences in enzymatic degradation susceptibility between the flange and the shaft can be determined (see Table 1 infra). Not wishing to be bound to any particular hypothesis, this difference in auto-fluorescence appears to be related to compositional differences between the two separate structures and indicates why differences in enzymatic degradation susceptibility are observed as shown in Table 1. Additional support for different auto-fluorescence in Hemiptera can be found in the brown planthopper (Wang, Tang et al., 2008, supra).

As demonstrated in the examples, infra, various proteases are extremely effective in degrading already synthesized sheaths even though carbohydrates are the primary component of stylet sheaths. Infra-red spectroscopy analysis of pure stylet sheaths indicates an IR absorption profile that is consistent with that of starch or cellulose (both glucan polymers). NMR analysis of intact and proteinase K treated (proteinase K completely dissolves D. citrus salivary sheaths) stylet sheaths reveal the presence of chemical shifts that do not originate from any carbohydrate and are likely from protein. These signals are significantly reduced when proteinase K treated stylet sheaths are dialyzed against deionized water. Composition and linkage analysis of purified salivary sheaths reveal the presence of glucose (~90% of total carbohydrate identified) and smaller quantities of mannose and xylose. The main sugar residue is 4-linked Glcp (82%). Branching 4.6-Glcp (3%) and terminal Glcp (3%) are present. The PMAA analysis (see Example 7, infra) indicates the presence of small amounts of 4-Manp and 4-Xylp. Therefore, the majority of the stylet sheath shaft/branching composition for D. citri is a glucan with 90% of the glucose molecules being linked by alpha-(1-4)-linkages and containing some beta-(1-4)-linkages. These results are consistent with a primary glucan composition of the sheaths that is solidified after secretion by crosslinking with a proteinaceous crosslinker. Thus, some proteases can destroy the stylet sheaths by degrading the proteinaceous crosslinker.

Furthermore, proteomic analysis (by Orbitrap, see Example 3 infra) of the sheaths has led to the identification of peptide fragments matching a gene with very high homology to laccase enzymes. Searching the D. citri genome database resulted in the identification of the cognate gene for this laccase. Laccases can act as polymerizing enzymes crosslinking peptides and polysaccharides. Laccases are copper containing enzymes. As part of this invention, it is determined that EDTA and other metal chelators, especially copper chelating compounds, can inhibit sheath formation. Upon discover of the laccase enzyme, ammonium tetrathiomolybdate, an inhibitor of laccase enzyme activity, is also determined to be a potent inhibitor of D. citri sheath formation (see below).

The discovery of the stylet sheath shaft/branching composition and a mode of polymerization leads to the development of compositions and methods for (1) controlling/preventing/reducing hemipteran insect damage to economically important plants described herein; and (2) preventing/reducing the transmission of vascular associated diseases to economically important plants.

For purposes of the invention, the following are definitions of certain terms used herein.

As used in the specification and claims, the singular form "a", "an", and "the" include plural references unless the context clearly dictates otherwise. For example, the term "a cell" includes both a single cell and a plurality of cells, including mixtures thereof.

"ACP SS" and "ACP SSs" means Asian citrus psyllid stylet sheath and Asian citrus psyllid stylet sheaths. D. citri is an example of an Asian citrus psyllid.

The terms "isolated", "purified", and "biologically pure", as used herein, refer to material that is substantially or essentially free from components that normally accompany it as found in its native state. In an exemplary embodiment, purity and homogeneity are determined using analytical chemistry techniques such as, but not limited to, polyacrylamide gel electrophoresis or high performance liquid chromatography.

The compositions of this invention can contain an agriculturally acceptable carrier, optionally an adjuvant, and one or more proteins and/or one or more small molecules. The protein(s) of this invention can be an enzyme (such as proteases and/or carbohydrate-degrading enzymes). The proteases and carbohydrate-degrading enzymes can block, inhibit, or reduce stylet sheath formation and/or degrade already formed stylet sheaths. Non-limiting examples of proteases of this invention include Flavourzyme® (protease from *Aspergillus oryzae*) (Novozymes, Inc., Franklinton, N.C.) proteinase K, carboxypeptidase, chymopapain, papain, ficin and other cysteine endopeptidases, bromelain, calpain, caspase, cathepsin, actinidin, tobacco etch virus (TEV) protease, and γ-glutamyl hydrolase. The carbohydrate-degrading enzymes include, but are not limited to, cellulase, hemicellulase, glucuronyl hydrolase, lytic polysaccharide monooxygenases, β-1,4-endoglucanase, amyloglucosidase, laminarinase and other endo-1,3(4)-β-glucanases, endodextranase, α-amylase, licheninase, xylanase, and mannan-degrading hydrolases. The small molecule(s) of the present invention can include, but are not limited to, compounds that inhibit or reduce the activity of one or more enzymes that produce the stylet sheaths. Non-limiting examples of such compounds that inhibit or reduce the activity of one or more enzymes that produce the stylet sheaths include EDTA, ammonium tetrathiomolybdate, D-penicillamine, 2,3,2-tetramine, 2,2,2-tetramine, 1,4,8,11-tetraazacyclotetradecane-1,4,8,11-tetraacetic acid (TETA), N,N',N"-tris(2-pyridylmethyl)-1,3,5-cis,cis,-triaminocyclohexane (tachpyr) and related compounds, and other metal-chelating compounds (and more specifically, copper-chelating compounds), and BAPN, dithiothreitol solution (DDT), nitrilotriacetic acid trisodium salt, 4-hydroxybenzyl alcohol, and kojic acid. Small molecules which inhibit the formation of stylet sheaths through unknown mechanisms include, but are not limited to, naringin, didymin, eriodictyol, eriocitrin, hesperetin, naringenin, 7-hydroxy-coumarin, limonin, limonin glucoside, and nomilin.

As used herein "in amounts effective" or "an effective amount" refer to the amount of the protein (protease and/or carbohydrate-degrading enzyme,) and/or small molecule (metal chelating agent or other compound described above and below) formulation administered (applied to, sprayed on, or otherwise administered) to a plant wherein the effect of the administration acts to at least reduce the ability of hemipteran insects to damage plants by at least reducing or preventing the insect's ability to form a stylet sheath in order to feed on the plant or to dissolve an already formed stylet sheath. By reducing or preventing the insect's ability to form a stylet sheath, one reduces or prevents the insect from feeding on the plant and thus prevent or reduce the transmission of vascular associated diseases to the plants for which the insect is a carrier or vector. By degrading or dissolving an already formed stylet sheath, one reduces the chance of transmission of vascular associated diseases to the plants for which the insect is a carrier or vector. Applying an effective amount of the compositions of this invention is that amount of the composition necessary to reduce or prevent transmission of the vascular associated disease pathogen from the insect to the plant or from the plant to the insect.

It is envisioned that functional formulations will contain adjuvants of any type specific to the active ingredient being administered. These adjuvants can include, but are not limited to, buffers, penetrating agents, surfactants, oils, and humectants. A buffer may be employed for the enzymes/proteins/small molecules of the present invention in view of the fact that enzymes/proteins/small molecules may be pH sensitive and need protection from potentially damaging variation in pH. It is possible that the natural pH of an economically important plant will be within the acceptable pH range of the enzyme/protein/small molecule being applied to it. In such instances, a buffer may not be required. Yet, in other cases, the natural pH of the economically important plant will be higher or lower of the optimal pH for a particular enzyme/protein/small molecule's activity. In such a case, a buffer may be useful to help achieve the desired activity.

When pH regulation is not important, such as when the natural pH of the economically important plant corresponds to the pH at which the applied enzyme/protein/small molecule is active, water may serve as the carrier. Where a buffer is employed, any buffer solution can be used which is compatible with the enzyme/protein/small molecule and does not deleteriously affect the plant that is being treated. Furthermore, the buffer is a material that is known to be safely used on some economically important plants, or at least on the economically important plant being treated. Examples of suitable buffers include, but are not limited to, an approximately 5 mM to approximately 50 mM solution of sodium succinate, sodium phosphate, potassium phosphate, sodium citrate, and/or Tris. In another embodiment, the concentration of the buffer can range from approximately 0.5 mM to approximately 500 mM. A buffer can include one or more surfactants, penetrants, and/or humectants that are compatible with the enzymes/protein/small molecules being applied, do not deleteriously affect the plant being treated, and are safely used on some economically important plants, or at least on the economically important plant being treated. Non-limiting examples of surfactants include Tween-80 and Triton X-100 and various commercial formulations of agricultural surfactants containing one or a combination of chemicals that could include, but are not be limited to, alcohol alkoxylates, alkylaryl ethoxylates, fatty amine ethoxylates, and organo-silicones. Surfactants can be charged or non-ionic surfactants. Non-limiting examples of oils include petroleum oils and vegetable oils. Non-limiting example of humectants includes glycerol.

A penetrating agent (a penetrant) can be any compound which causes or assists the protein, enzyme, and/or small molecule to enter the cuticle layer of the plant. For some proteins, enzymes, and/or small molecules, the penetrating agent can be a surfactant, humectant, or the like which further enhances the efficiency of the invention. Surfactants, humectants, and the like are employed in order to wet the surface of the plant and help keep on the plant the enzyme, protein, and/or small molecule that is being applied to the plant. Some of the enzymes, proteins, and/or small molecules useful in the present invention may be capable of entering or passing through the cuticle layer of the plant without a penetrating agent. However, a penetrating agent may enhance the efficiency of the enzyme's or protein's or small molecule's entry into the cuticle layer. For the small molecules useful in the present invention, the penetrating agent can include, but is not limited to, cutinase, wax esterase, and exoenzyme which are capable of entering or penetrating the cuticle layer faster or more efficiently than the small molecule and which will aid or speed the entry of the small molecule into the cuticle layer of the plant. Further examples of appropriate penetrating agents can be selected from materials known in the art as adjuvants for agricultural chemicals.

As used herein, the term "agriculturally acceptable" includes agricultural, industrial and residential uses which are compatible with plants.

As used herein, the term "agriculturally acceptable carrier" includes any liquid carrier to which the enzymes, proteins, and/or small molecules of the present invention can be added and is not harmful to the enzymes, proteins, and/or small molecules of the invention or the plants to which it is being applied. In one embodiment, an agriculturally acceptable carrier excludes hemipteran insects and/or their body parts and the pathogen causing the disease to be treated or prevented. In another embodiment, adjuvants, buffers, penetrating agents, surfactants, and humectants exclude hemipteran insects and/or their body parts and the pathogen causing the disease to be treated or prevented. In a further embodiment, the proteins, enzymes, and small molecules; while possibly present in hemipteran insects and/or the pathogen which cause the disease to be treated or prevent; such proteins, enzymes, and small molecules are not be administered to the plant be treated by such hemipteran insect and/or pathogen. Rather, in this embodiment, the compositions containing such proteins, enzymes, and/or small molecules are being applied or administered to the plants in need of treatment by a human, either directly or indirectly, and not by the insect, directly or indirectly. In an alternative embodiment, a recombinant hemipteran insect or recombinant pathogen can be made to produce one or more of proteins, enzymes, and/or small molecules described herein and thus the recombinant organism its body parts) be can used to administer or apply to the plant the one or more of proteins, enzymes, and/or small molecules described herein. In this embodiment the recombinant organism could be a considered an agriculturally acceptable carrier and included in the compositions described herein.

As used herein, a plant is defined as any monocotyledonous or dicotyledonous plant, and can be any plant of interest in agriculture, horticulture, or wood culture, such as crop plants, leguminous plants, oil producing plants, fruit producing plants, starch producing plants, fruit producing trees, nut producing trees, ornamental plants and trees, etc. An "economically important plant" is a plant (monocot or dicot) which is useful for humans and/or other animals. Economically important plants can be useful for food for humans and/or other animals, for production of industrial products (such as paper, lumber, fuel, etc.), for ornamental purposes, for agriculture, for horticulture, for aquaculture, for wood culture, etc. While not every plant is an economically important plant, most plants are economically important plants.

As used herein "vascular associated diseases" are diseases which adversely impact the vascular system (xylem and/or phloem) of a plant and cause damage and/or death to a plant. Vascular associated diseases can be caused by bacteria, viruses, or other microorganisms. Many such diseases are transmitted by Hemiptera. Non-limiting examples of vascular associated disease include bacterial diseases including citrus greening disease, caused by the phloem limited bacterium 'Candidatus' Liberibacter species. Other phloem limited bacterial diseases include papaya bunchy top disease, the cucurbit yellow vine disease, and the clover club leaf disease. Peirces disease in grapes and citrus variegated chlorosis in citrus are examples of diseases caused by xylem limited *Xylella* bacterial species vectored by xylem feeding hemipteran insects including leafhoppers (Cicadellidae: Cicadellinae) and spittlebugs (Cercopidae). Other diseases caused by xylem-inhabiting bacteria and transmitted by salivary sheath forming hemipteran insects (SSFHI) including phony peach, plum leaf scald, almond leaf scorch, bacterial leaf scorch of coffee, oak leaf scorch, and leaf scorch diseases of oleander, pear, maple, mulberry, elm, sycamore, and miscellaneous ornamentals, and alfalfa dwarf disease. Other plant vascular limited organisms include molicutes (prokaryotic organisms that do not have a cell wall) most of which belong to the genus *Phytoplasma* or *Spyroplasma*. Asters yellows, tomato big bud, apple proliferation, pear decline, lethal yellowing of coconut palm, corn stunt, and citrus stubborn disease are all diseases caused by these microorganisms that are transmitted by SSFHI. Phloem-residing plant pathogenic protozoa (unicellular eukaryotes) can be transmitted by stink bugs (these are SSFHI) causing disease such as phloem necrosis of coffee, heartrot of coconut palms and sudden wilt of oil palms.

More than one-half of known plant viruses are transmitted from diseased plants to healthy plants by insects, and many are phloem-limited or phloem associated. The most important group of virus vectoring insects include the SSFHI such as the aphids (Aphididae, 192 species, 275 viruses), leafhoppers (Cicadellidae, 49 species, 31 viruses), the planthoppers (Fulgoroidea, 28 species, 24 viruses), the whiteflies (Aleurodidae, 3 species, 43 viruses), the mealybugs (Pseudococcidae, 19 species, 10 viruses), and some treehoppers (Membracidae, 1 species, 1 virus) (See Agrios, George N. "Transmission of Plant Diseases by Insects." *Encyclopedia of Entomology*. Springer Netherlands, 2291-2317, 2005).

Unless defined otherwise, all technical and scientific terms used herein have the same meaning as commonly understood by one of ordinary skill in the art to which the invention belongs. The terms "about" and "approximately" are defined as plus or minus ten percent; for example, about 100° F. means 90° F. to 110° F. Although any methods and materials similar or equivalent to those described herein can be used in the practice or testing of the present invention, the preferred methods and materials are now described.

The present invention demonstrates that the salivary sheaths can be degraded or prevented from solidifying by enzymatic and non-enzymatic methods. Furthermore, the compositions and method of treating of the present invention disrupt preformed/nascent hemipteran stylet sheath, and/or deter or block hemipteran insects from feeding on plants. Several classes of enzymes (proteases and carbohydrate-degrading enzymes) are useful in the present invention. Examples include, but not limited to, cellulase from *Aspergillus* (Sigma-Aldrich, St. Louis, Mo.), Flavourzyme® (protease from *Aspergillus oryzae*) (Sigma-Aldrich, St. Louis, Mo.), carboxypeptidase W from wheat (Sigma-Aldrich, St. Louis, Mo.), chymopapin from papya latex (Sigma-Aldrich, St. Louis, Mo.), papain from papaya latex (Sigma-Aldrich, St. Louis, Mo.), bromelain from pineapple stem (Sigma-Aldrich, St. Louis, Mo.), ficin from fig (Sigma-Aldrich, St. Louis, Mo.), proteinase K (Thermo Fisher Scientific, Inc., Waltham, Mass.), amyloglucosidase (Sigma-Aldrich, St. Louis, Mo.), α-amylase (Sigma-Aldrich, St. Louis, Mo.), laminarinase (MP Biomedicals, LLC, Santa Ana, Calif.), licheninase I (C5•6 Technologies, Inc., Middleton, Wis.), etc. Useful small molecules for non-enzymatic degradation or inhibition of sheath formation include, for example, 3-aminopropionitrile fumarate salt (also known as BAPN, β-alaninenitrile) (Sigma-Aldrich, St. Louis, Mo.), dithiothreitol solution (also known as DDT) (Sigma-Aldrich, St. Louis, Mo.), nitrilotriacetic acid trisodium salt (Sigma-Aldrich, St. Louis, Mo.), 4-hydroxybenzyl alcohol (Sigma-Aldrich, St. Louis, Mo.), kojic acid (Sigma-Aldrich, St. Louis, Mo.), ammonium tetrathiomolybdate (Sigma-Aldrich, St. Louis, Mo.), ethylenediaminetetraacetic acid (EDTA, Sigma-Aldrich, St. Louis, Mo.) and/or other metal chelating agents. Other small molecules which inhibit the formation of stylet sheaths through unknown mechanisms and which are considered GRAS (generally regarded as safe) include, but are not limited to, naringin, didymin, eriodictyol, eriocitrin, hesperetin, naringenin, 7-hydroxycoumarin, limonin, limonin glucoside, and nomilin.

Methods for using these proteins (proteases and/or carbohydrate-degrading enzymes) and/or small molecules to inhibit the formation of hemipteran stylet sheaths or degrade hemipteran stylet sheaths that have already been formed, disrupt preformed/nascent hemipteran stylet sheath, and/or deter or block hemipteran insects from feeding on plants, include spraying the compositions onto plants. In general, the composition of this invention can be applied to any economically important plant species in accordance with techniques well known to persons skilled in the art, such as, in the form of a spray. A spray can be prepared by mixing the protein(s) and/or small molecule(s) and, optionally, one or more penetrating agents into a suitable carrier, such as a buffer solution. The compositions and formulations of the invention can be applied to at least one plant by various techniques that are well-known to one of ordinary skill in the art, including, but not limited to, sprays, sprinklers, drips, dips, drenches, dressings, oils, and any type of irrigation system. As non-limiting examples, the invention encompasses foliar sprays and turf sprays. As non-limiting examples, the methods include spraying, dipping, dripping, and drenching the compositions and formulations of this invention onto plants. In another embodiment, applying the composition to the plant involves any method in which one or more roots uptake the compositions described herein, such as injecting the composition into the soil, or spraying, dripping or drenching the composition onto the soil via an irrigation system. In another embodiment, one can apply the compositions to the plant by injecting the composition into the plant. Alternatively, the composition can be applied to the surface of the plant (to the leaves, stems, branches, trunk, etc.) by spraying or dripping the composition onto the plant.

The amount of protein and/or small molecule in the total composition including the carrier is defined as an amount effective to at least reduce the formation of stylet sheaths in a feeding insect or at least increase the enzymatic breakdown of stylet sheaths in insects already feeding on said plant, or disrupt preformed/nascent hemipteran stylet sheath, and/or deter or block hemipteran insects from feeding on plants, or to reduce or prevent transmission of vascular associated diseases from the insect to the plant or from the plant to the insect. For enzymes, an example of an effective amount ranges between approximately 0.01 unit enzyme/1 µl composition to approximately 100,000 units enzyme/1 µl composition. In an alternative embodiment, the amount of enzyme can range from approximately 1 units enzyme/1 µl composition to approximately 10,000 units enzyme/1 µl composition. In another embodiment, the amount of enzyme can range from approximately 100 units enzyme/1 µl composition to approximately 1,000 units enzyme/1 µl composition. For other proteins, the amount of protein in the composition can range from approximately 0.001 mM to approximately 1 M, or approximately 0.1 mM to approximately 100 mM, or approximately 1 mM to approximately 10 mM of the composition. The concentration range for small molecules in the composition is similar to the concentration range for proteins; i.e., from approximately 0.001 mM to approximately 1 M, or approximately 0.1 mM to approximately 100 mM, or approximately 1 mM to approximately 10 mM of the composition. It is recognized that amounts outside these ranges are acceptable, depending upon the enzyme/protein/small molecule being applied to the plant and the plant being treated. The amount of a surfactant, if included in the composition, is readily ascertainable by persons skilled in the art and will typically range from between about 0.01% to about 90% by weight based on the weight of the carrier or between approximately 0.1% to approximately 10% by weight based on the weight of the carrier.

The following examples are intended only to further illustrate the invention and are not intended to limit the scope of the invention as defined by the claims.

EXAMPLE 1

Figure 2A:
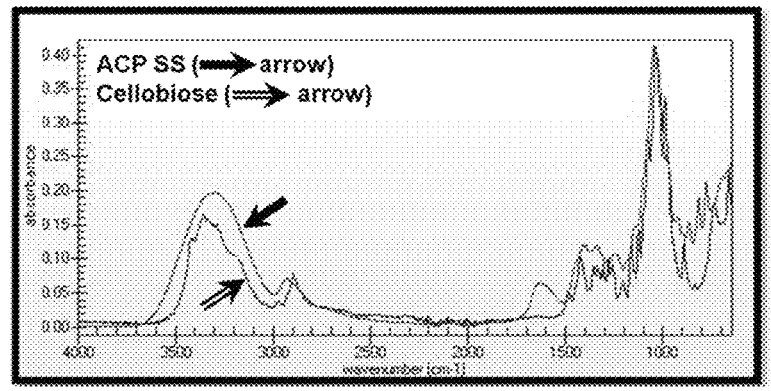
FIGS. 2A-2D are Fourier Transform infrared spectra (FTIR) of isolated Asian citrus psyllid (ACP) SSs.
Figure 2B:
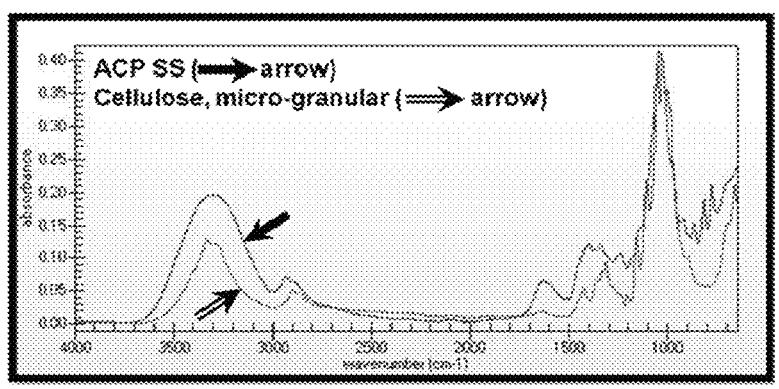
Figure 2C:
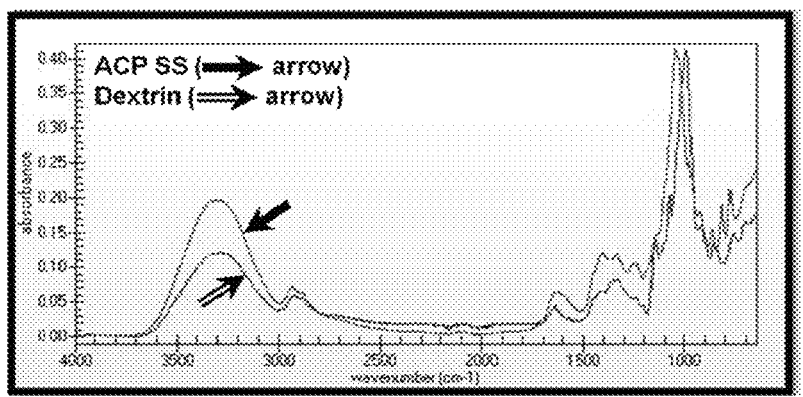
Figure 2D:
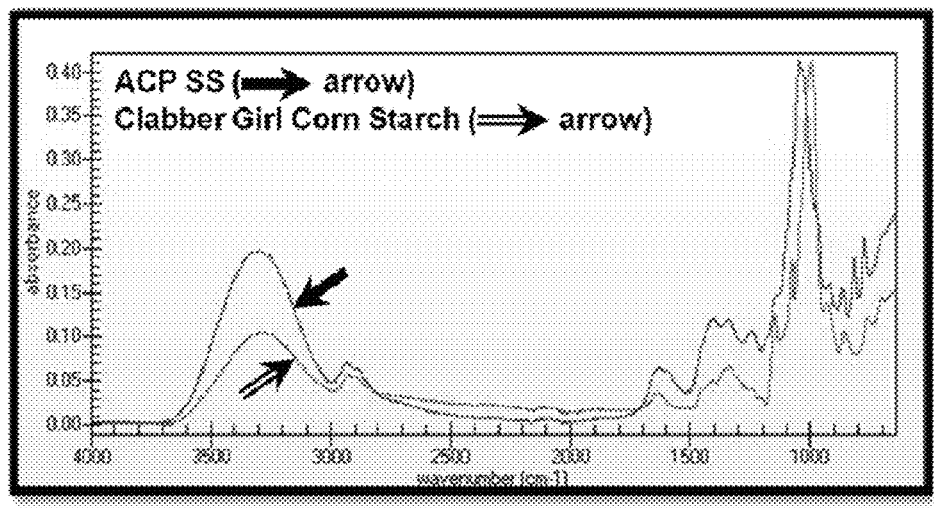
Figure 2E:
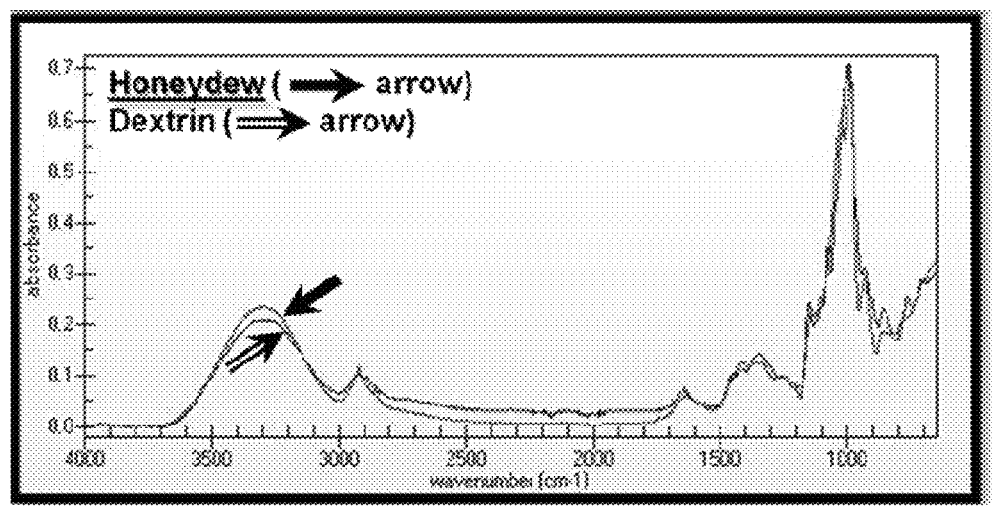
FIG. 2E is a FTIR of isolated ACP honeydew also showing carbohydrate as the major component of sheaths and honeydew produced from ACP. Diamond attenuated total reflectance (ATR) infrared spectra of ACP SSs, FIG. 2A-2D, or Asian citrus psyllid honeydew.

Fourier transform infrared spectroscopy (FT-IR) analysis was performed on ACP SSs and indicated glucans to be a major component of ACP SSs (see FIG. 2B). This FT-IR analysis was performed using ACP SSs isolated from MFCs (as described by Morgan et al 2013, supra). These ACP SS were placed onto the diamond ATR component of a Nicolet™ iN™10 infrared microscope (Thermo Scientific, Waltham, Mass.) and scanned by FT-IR. The spectra were collected and analyzed by OMNIC™ Software (Thermo Scientific, Waltham, Mass.) and compared to known samples of cellobiose (Sigma Aldrich, St. Louis, Mo.) (see FIG. 2A), cellulose (Sigma Aldrich, St. Louis, Mo.) (see FIG. 2B), dextrin (Sigma Aldrich, St. Louis, Mo.) (see FIG. 2C), corn starch (Clabber Girl, Hulman & Company, Terre Haute, Ind.) (see FIG. 2D). The ACP SSs are designated by a solid arrow in FIGS. 2A through 2D; the known samples are designated by a striped arrow. Regions of interest corresponding to either the O—H bond or the C—O single bond regions are approximately 3200-3600 $cm^{-1}$ and approximately 1150-950 $cm^{-1}$ wavenumbers, respectively. The pattern of the spectra in the C—O region (1150-950 $cm^{-1}$) indicates a correlation to the glucans that were tested. Because glucans are a major component of ACP SSs, the effects of carbohydrate-degrading enzymes on stylet sheaths are explored. In this example, cellulase (Sigma #C2605, Sigma-Aldrich, St. Louis, Mo.) is tested on preformed ACP SSs as the correlation between cellobiose and cellulose from the FT-IR analyses indicates a correlation in the C—O region (FIGS. 2A and 2B, respectively), suggesting a similar structure between ACP SSs and these glucans. FIG. 2E illustrates a comparison of ACP honeydew to dextrin that indicates that carbohydrate is the major component of honeydew from ACP. However, when compared to FIG. 2C at approximately 1150-950 $cm^{-1}$ wave numbers (the C—O single bond region), there is no shift, thus indicating that the SS composition is structurally different than honeydew (an alternate ACP bodily secretion).

In order to test cellulase's effect on preformed ACP SSs, formed, solidified stylet sheaths were harvested directly from the surface of an MFC membrane (in these experiments either plastic wrap or parafilm was used) as described herein and in Morgan et al. 2013, supra. Approximately 100 psyllids were placed into an MFC for about 24 hours. The MFCs consisted of *D. citri* caged individually and/or in groups within 100 mm×15 mm plastic Petri dishes. A single kitchen plastic wrap layer was stretched across the top of each Petri dish to seal the Petri dish from insect escape and to provide a stylet penetrable surface for insect probing.

Several MFCs (the Petri dishes covered with kitchen plastic wrap or parafilm and containing *D. citri*) were placed into clear Pyrex® baking dishes with the membrane (kitchen plastic wrap or parafilm) side up, and the Pyrex® baking dish is covered with a single layer of clear kitchen plastic wrap to prevent external contaminant interactions with the membrane surface during incubation. MFCs were incubated at a temperature of about 25° C., relative humidity of about 75%, and a light:dark cycle of about 14:1. Collection of partial stylet sheaths, shaft/branching portions without the flange, was performed using deionized water applied directly to the sheath surface to wash the surface of the MFC, and then the application of approximately 100 µl of an approximately 50 mM sodium phosphate buffer at a pH of approximately 6.0 for direct harvest of partial sheaths from the membrane surface using a bent glass rod to scour the plastic wrap surface to dislodge the stylet sheaths. The sodium phosphate buffer containing dislodged sheath shafts was removed using a pipette and placed in a microcentrifuge tube (1.5 ml tube), and cellulase (Sigma #C2605, Sigma Aldrich, St. Louis, Mo.) was added by ratio at approximately 1 part cellulase to 25 parts sodium phosphate buffer (approximately 1:25 ratio). Approximately 15 µl was then transferred to a pre-cleaned glass slide (Fisher, #12-550-19, Thermo Fisher Scientific, Inc., Waltham Mass.), covered with a premium cover slip, and edges sealed using clear nail polish CG, 3INI NL #Q004 SHN ON (CoverGirl, Hunt Valley, Md.) to keep the buffer from evaporating during incubation. This slide was then placed in an approximately 60° C. incubator of about 72 hours and observed at about 24 hour intervals.

Figure 3A:
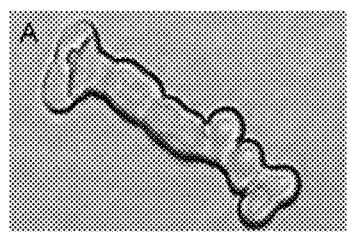
FIGS. 3A-3F are micrographs demonstrating *D. citri* purified stylet sheaths susceptibility to the cellulose degrading enzyme, cellulase (Carazyme®) at pH approximately 6.0 at about 60° C. for about 72 hours.
Figure 3B:
Figure 3C:
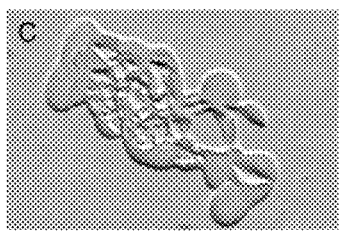
Figure 3D:
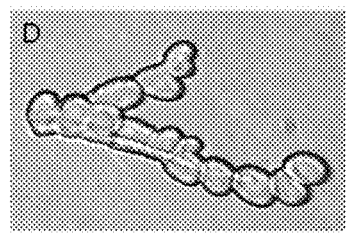
Figure 3E:
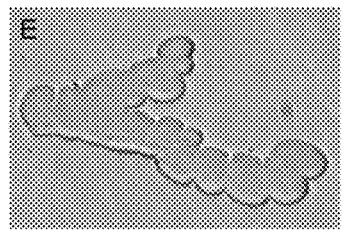
Figure 3F:
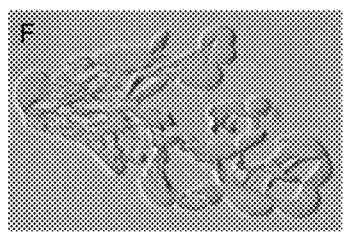
Figure 3G:
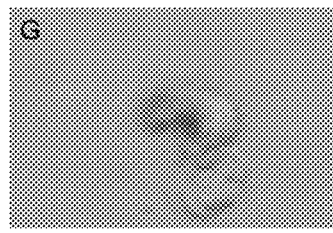
FIGS. 3G 3I are micrographs of malformed stylet sheath when *D. citri* attempt to feed on a liquid diet containing approximately 1:1000 dilution of cellulase.
Figure 3H:
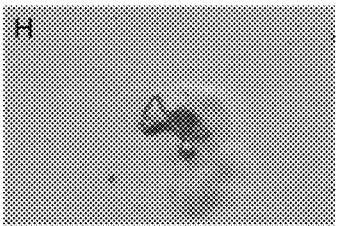
Figure 3I:
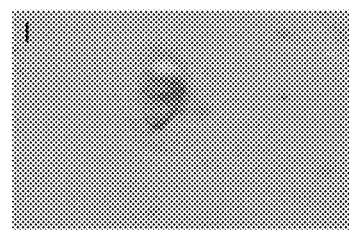

FIGS. 3A, 3B, and 3C and FIGS. 3D, 3E, and 3F are light micrograph pictures of repeated experiments representing separate treatment of two salivary sheaths. FIG. 3A and FIG. 3D are separate salivary sheaths prior to the addition of cellulase. FIG. 3B and FIG. 3E are the same sheaths, respectively, after 72 hours incubation with cellulase. FIG. 3C and FIG. 3F are the same sheaths, respectively, when gentle pressure was applied to the coverslip over the sheaths that had been incubated with cellulase for 72 hours. After the 72 hours of incubation with cellulase, the sheaths were swollen and less defined by light defraction as seen before the incubation. Fracture of the sheaths is clearly visible in FIGS. 3C and 3F after gentle pressure was applied indicating loss of integrity caused by the cellulase (no swelling or fracturing was observed in sheaths incubated in the same manner but without cellulase, data not shown). Similar results were observed for cellulase incubations as short as 30 minutes (data not shown). Because of the observed result with cellulase, sheath degradation experiments as described above for cellulase were performed using a number of polysaccharide-degrading enzymes and proteases. Table 1 shows the results for each of these enzymes and for cellulase as a comparison. Both carbohydrate-degrading enzymes and proteases were effective at degrading the sheaths. Note that the protease Flavourzyme was tested against isolated sheaths from both the Asian citrus psyllid (*D. citri*) and the whitefly (*Bemisia tabaci* B biotype), and it was shown to be effective at degrading sheaths from both insects. These results demonstrate that sheaths contain both carbohydrates and proteins that are necessary for structural integrity. Interestingly, not all the polysaccharide-degrading enzymes and proteases worked equally well providing insight into sheath structural properties. The α-amylase specifically degraded the flange, a result that supports auto-fluorescent findings of structural differences between the flange and the shaft (See FIGS. 1A through 1D). Dextrinase hydrolyzes α-(1,6)-alpha-glucosidic bonds and does not affect sheath integrity; whereas cellulase and amyloglucosidase (which hydrolyzes α-D-(1-4), α-D-(1-6), and α-D-(1-3)-glucosidic bonds) adversely impact stylet sheath integrity, albeit in different manners.

TABLE 1

| Name/Supplier & Catalogue #/EC Number | Activity/Type | Organism Tested* | Inhibition of Sheath Formation | Sheath Degradation |
|---|---|---|---|---|
| Cellulase from *Aspergillus* species Sigma #C2605 EC #: 232-734-4 | Degrades cellulose | *D. citri* | +++++ (*D. citri*) | +++ (*D. citri*) |
| Protease Flavourzyme ® from *Aspergillus oryzae* Sigma #P6110-50 mL EC #: 232-752-2 | Endopeptidase and exopeptidase protease mix | *D. citri* and WF | +++++ (*D. citri*) +++++ (WF) | +++++ (*D. citri*) +++++ (WF) |
| Dextrinase from *Chaetomium erraticum* Sigma #D0443-50 mL EC #: 232-803-9 | Endodextranase that hydrolyzes α-(1,6)-alpha-glucosidic linkages in dextran | *D. citri* | Not Done | – |
| α-Amylase from *Aspergillus oryzae* Sigma #A8220-50 mL EC #: 232-588-1 | Hydrolyses alpha-bonds of large alpha-linked polysaccharides | *D. citri* | Not Done | ++ Flange degrade; not sheath |
| Amyloglucosidase from *Aspergillus niger* Sigma #A7420 EC #: 232-877-2 | Hydrolyses α-D-(1-4), the α-D-(1-6), and the α-D-(1-3) glucosidic bonds of oligosaccharides | *D. citri* | Not Done | ++ Sheaths swell excessively |
| Ficin from fig tree latex Sigma #F6008 EC #: 232-599-1 | Cysteine endopeptidase | *D. citri* | +++++ Reduced feeding & No sheaths | +/− |
| Carboxypeptidase W from wheat Sigma #C6742 EC #: 3.4.16.6 | Serine carboxypeptidase C (exopeptidase) | *D. citri* | +++++ | +++++ |
| Chymopapain from papaya latex Sigma #C8526-250UN EC #: 232-580-8 | Cysteine peptidase | *D. citri* | +++++ | +++++ |
| Papain from papaya latex Sigma #P5306-25 mg EC #: 232-627-2 | Cysteine peptidase | *D. citri* | ++++ | ++ |
| Bromelain from pineapple stem Sigma #: B5144-100UN EC #: 253-387-5 | Cysteine peptidase | *D. citri* | +++++ | +++++ |
| Trypsin from bovine pancreas Sigma #: T8658-1VL EC #: 232-650-8 | Serine peptidase | *D. citri* | – | – |
| Collagenase Type VII from *Clostridium histolyticum* Sigma #: C0773-1.5KU EC #: 232-582-9 | Degrades peptide bond in collagen | *D. citri* | Not Done | – |
| Laminarinase MP Biomedicals LLC #02198904 EC #: 3.2.1.6 | Endo-1,3(4)-β-glucanase catalyzes the endohydrolysis of 1,3- or 1,4-linkages in β-D-glucans | *D. citri* | Not Done | +++ |

TABLE 1-continued

| Name/Supplier & Catalogue #/EC Number | Activity/Type | Organism Tested* | Inhibition of Sheath Formation | Sheath Degradation |
|---|---|---|---|---|
| Licheninase C5·6 Technologies, Inc. #30652-1 EC #: 3.2.1.73 | Hydrolysis of (1->4)-beta-D-glucosidic linkages in beta-D-glucans containing (1->3)- and (1->4)-bonds | D. citri | Not Done | +++ |
| β-(1→3)-D-Glucanase from Helix pomatia Sigma #67138-10 mg EC #: 232-927-3 | Digest β-1,3-glucan | D. citri | Not Done | – |
| Proteinase K from Tritirachium album Fischer #BP1700-100 EC #: 3.4.21.64 | Broad protease specificity | D. citri | Not Done | +++++ |

D. citri = Diaphorina citri, Asian citrus psyllid
WF = Bemisia tabaci, B biotype, whitefly
'–' = No effect apparent
'+/–' = inconclusive
'+' = apparent slight effect
'++' = increased apparent effect
'+++' = high effect
'++++' = very high effect
'+++++' = complete degradation of sheaths or inhibition of sheath synthesis

EXAMPLE 2

The next step was to determine if addition of cellulase to the diet of D. citri would interfere with stylet sheath formation. A D. citri diet is prepared as described by Hall, David et al., "Research toward an artificial diet for adult Asian citrus psyllid," Annals of the Entomological Society of America 103.4:611-617 (2010). Approximately 25 D. citri were collected into polystyrene Cellstar 35 mm×10 mm dishes (Griener Bio-One, Monroe, N.C.) that were then sealed using a single layer of Parafilm® M (Pechiney Plastic Packaging Company, Chicago, Ill.). Approximately 99 µl of liquid ACP diet (e.g., diet lacking the solidifying agar component, see Hall, et. al., 2010, supra) was mixed with approximately 1 µl of cellulase (Sigma Aldrich, St. Louis, Mo.) and mixed. Approximately 100 µl of this mixed liquid diet containing cellulase was then added to the single layer Parafilm® M surface, which was then covered with another layer of Parafilm® M to form a sandwich (e.g., Parafilm® M—liquid ACP diet with cellulase—Parafilm® M) to allow ACP to feed into the liquid ACP diet containing cellulase. This MFC was then incubated at about 25° C., at about 75% relative humidity, with a light:dark cycle of approximately 14:10 hours for a period of about 24 hours. After about 24 hours, the stylet sheaths were observed using an inverted microscope. FIGS. 3G through 3I are images of three separate locations where *D. citri* made attempts to feed into the liquid ACP diet containing approximately 1 unit/µl cellulase. As seen in FIGS. 3G, 3H, and 3I, the ACP SSs were not able to form in the presence of cellulase. See Table 1, supra, for a summary of the results of this example using cellulase.

EXAMPLE 3

Because many biomolecule polymerizing enzymes require divalent cations as cofactors, the effect of ethylenediaminetetraacetic acid (EDTA), a chelator of divalent cations, on ACP SS formation was tested by adding EDTA to the previously described liquid ACP diet (see Hall et al., 2010, supra). The EDTA was added to the liquid ACP diet at a concentration of approximately 2 mM EDTA in $diH_2O$. Approximately 200 *D. citri* were placed in plastic Petri dishes. The dishes were covered with a single layer of Parafilm® M to form MFC. Approximately 2 ml of the liquid ACP diet containing approximately 2 mM solution of EDTA/$diH_2O$ was added to the surface of the Parafilm® M, and this solution was then covered with another layer of Parafilm® to form a sandwich of Parafilm® M-liquid ACP diet containing EDTA/$diH_2O$-Parafilm® M. Additionally, a negative control MFC plate was set up that had liquid ACP diet only. The MFC plates were incubated at a temperature of about 25° C., a relative humidity of about 75%, and a light/dark cycle of about 14:10 hours duration. Following the 24-hour incubation, the fluid (either liquid ACP diet containing EDTA or just the liquid ACP diet) between the two sheets of plastic was harvested by using a sterile 5 ml syringe and 20-gauge needle which was pushed into the center of the Parafilm® M-fluid-Parafilm® M sandwich, and the fluid was then removed by syringe plunger suction. The harvested fluids were put into sterile 50 ml conical vials, placed at about −80° C. until frozen. Each vial of harvested fluid was then lypholyzed overnight. The lyophilized product was then solubilized in approximately 15 µl conical vials, placed at about −80° C. until frozen, then each new vial was lyopholyzed overnight. The lyophilized product was then solubilized in approximately 15 µL of approximately 1× Laemmili buffer (Bio-Rad, Hercules, Calif.) containing approximately 5% 2-mercaptoethanol. The sample was loaded onto a sodium dodecyl sulfate polyacrylamide gel (SDS-PAGE) and underwent electrophoresis. The SDS PAGE gel was then stained with coomassie. Uncommon bands between the liquid ACP diet containing EDTA and liquid ACP diet without EDTA (negative control) lanes were cut out and analyzed by Orbitrap (Thermo Scientific, Waltham, Mass.) protein analysis, according to manufacturer's protocol.

The Orbitrap analysis showed the presence of glycine and proline rich proteins in the *D. citri* salivary sheath protein preparation in the MFC containing only the liquid ACP diet. This presence of glycine and proline rich proteins is a characteristic of collagen, a protein that is crosslinked into large polymers the activity of lysyl oxidase. Lysyl oxidase is an enzyme that has multiple known functions; its ability to crosslink collagen and elastin being most commonly known (Csiszar, K. Prog. *Nucleic Acid Re.* Volume 70, 1-32, 2001). A highly specific chemical inhibitor of lysyl oxidase is 3-aminopropionitrile fumarate salt (also known as BAPN).

To determine if BAPN had an inhibitory effect on stylet sheath formation, BAPN was added to liquid ACP diet (as described in Example 2 supra) at concentration of 100 mM and fed to *D. citri* as described above in Example 2. After about 24-hour incubation, *D. citri* feeding sites were observed. As seen in FIG. 4D, BAPN prohibited the solidification of the ACP SS as compared to stylet sheath formation for normal ACP SS formation as structurally exemplified in FIG. 4A (ACP SS isolated whole from a MFC containing Solvy™ membrane) or as exemplified in FIG. 4B (an ACP SS formed in the present of liquid ACP diet). See also Table 2 and Table 3, infra. Not wishing to be bound to any particular hypothesis, this evidence supports the hypothesis of enzymatically driven crosslinking involving proteins as part of the *D. citri* salivary sheath structure.

Based on the results of the BAPN experiment, similar experiments were performed using other small molecules (in lieu of BAPN, see table 2) to determine if these small molecules could inhibit ACP SS formation. The small molecules used in these experiments and the results are summarized in Table 2 infra. The concentration of these small molecules, water or a buffer were used (added to the liquid 2×ACP diet) to bring the final concentration to 1×, the pH, and temperature used in the experiments for each small molecule are presented in Table 3 infra.

TABLE 2

| Name/Supplier & catalogue #/EC number | Activity/Type | Inhibition of Sheath Formation |
|---|---|---|
| 3-aminopropionitrile fumarate salt (BAPN) Sigma #A3134-5G CAS #: 2079-89-2 | Specific inhibitor of collagen cross-linking enzyme (lysyl oxidase) | '+++++' (*D. citri*) '+++++' (WF) |
| Ethylenediaminetetraacetic acid (EDTA) Sigma #E6758 CAS #60-00-4 | Chelating agent used to sequester metal ions | '+++++' (*D. citri*) |
| Dithiothreitol Solution (DTT) Sigma #646563 CAS #3483-12-3 | Dithiothreitol is an effective reducing agent for protein analysis | '+++++' (*D. citri*) |
| Ammonium Tetrathiomolybdate Sigma #323446 CAS #15060-55-6 | Chelating agent used to sequester copper | '+++++' (*D. citri*) |
| Nitrilotriacetic acid trisodium salt Sigma #N0253 CAS #5064-31-3 | Chelating agent used to sequester metal ions | '+++++' (*D. citri*) |
| 4-hydroxybenzyl alcohol Sigma #W398705 CAS #623-05-2 | Tyrosinase inhibitor | '−' (*D. citri*) |
| Kojic Acid Sigma #K3125 CAS #501-30-4 | Laccase and Tyrosinase inhibitor | '++' (*D. citri*) |

*D. citri* = *Diaphorina citri*, Asian citrus psyllid
WF = *Bemisia tabaci*, B biotype, whitefly
'−' = No effect apparent inhibition of stylet sheath
'+/−' = inconclusive inhibition
'+' = apparent slight inhibition effect
'++' = increased apparent inhibition effect
'+++' = high inhibition effect
'++++' = very high inhibition effect
'+++++' = complete inhibition of sheath synthesis

TABLE 3

| Name/Supplier & catalogue #/EC number | Buffer | Concentration of Chemical in buffer | Conditions pH and Temp. |
|---|---|---|---|
| 3-aminopropionitrile fumarate salt (BAPN) Sigma #A3134-5G CAS #: 2079-89-2 | N/A | 50 mM | pH 7.4 Temp: 25° C. |
| Ethylenediaminetetraacetic acid (EDTA) Sigma #E6758 CAS #60-00-4 | N/A | 2.0 mM | pH 7.4 Temp: 25° C. |
| Dithiothreitol Solution (DTT) Sigma #646563 CAS #3483-12-3 | 50 mM HEPES | 25 mM | pH 6.7 Temp: 25° C. |
| Ammonium Tetrathiomolybdate Sigma #323446 CAS #15060-55-6 | 100 mM $KH_2PO_4$ | 2.5 mM | pH 6.5 Temp: 25° C. |
| Nitrilotriacetic acid trisodium salt Sigma #N0253 CAS #5064-31-3 | 25 mM HEPES | 5 mM | pH 6.7 Temp: 25° C. |
| 4-hydroxybenzyl alcohol Sigma #W398705 CAS #623-05-2 | 25 mM HEPES | 5 mM | pH 6.7 Temp: 25° C. |

TABLE 3-continued

| Name/Supplier & catalogue #/EC number | Buffer | Concentration of Chemical in buffer | Conditions pH and Temp. |
|---|---|---|---|
| Kojic Acid Sigma #K3125 CAS #501-30-4 | 25 mM HEPES | 5 mM | pH 6.7 Temp: 25° C. |

EXAMPLE 4

While not wishing to be bound to any particular hypothesis, based on the results of Examples 1, 2, and 3, it is hypothesized that the structure of the ACP SSs could include protein cross-links that are catalyzed by an enzyme with an oxidative role, an enzyme at least somewhat similar to a lysyl oxidase. To determine if a protein is associated with the identified glucan, proteases were tested in experiments similar to Examples 1 and 2 above. The following proteases were added individually in separate experiments (described infra) to membranes on which D. citri adults were previously allowed to first form sheaths in the absence of proteases: Flavourzyme® (a protease cocktail), carboxypeptidase W, chymopapain, bromelain, papain, ficin, licheninase, laminarinase, and β-(1→3)-D-glucanase. Carboxypeptidase W, chymopapain, bromelain, papain, and ficin were selected because they are naturally present in human edible plants and/or fruits. Licheninase, laminarinase, and β-(1→3)-D-glucanase were selected because glucan appears to be a major component of ACP SSs, as indicated by the FTIR analysis described supra and the NMR analysis described infra. For each experiment, approximately 25 D. citri adults were placed into polystyrene Cellstar 35 mm×10 mm dishes (Griener Bio-One, Monroe, N.C.) that were then sealed using a clear plastic wrap. The D. citri were allowed to mock feed in these MFCs for approximately 4 days or until all D. citri were dead, typically 4 to 5 days, incubated at about 25° C., a relative humidity of about 75%, and a light:dark cycle of about 14:10 hours. MFCs were maintained within clear Pyrex® baking dishes with the membrane (clear plastic wrap) side up, and the baking dish covered with a single layer of clear plastic wrap to prevent external contaminant interactions with the MFCs' membrane surface during incubation. After the incubation period, approximately 15 μl of each respective protease solution was added to each separate MFC directly to the clear plastic wrap membrane on the outer face of the MFC away from the ACP on the inside, according to the concentration and incubation conditions for each enzyme listed in Table 4, infra. Then each MFC was covered with premium glass cover slips (Fisher, #12-440-10, Thermo Fisher Scientific, Inc., Waltham, Mass.), and the edges were sealed using clear nail polish CG, 31N1 NL #Q004 SHN ON (CoverGirl, Hunt Valley, Md.) to keep the buffer/protease solution from evaporating during the incubation period. Fully formed ACP SSs from the negative control MFCs appear similar to the ACP SSs shown in FIGS. 4A and 4B from Example 3. FIG. 4C shows the digestion of a previously solidified ACP SS after treatment with Flavourzyme® for about 30 minutes, indicating that its structure has been degraded from a solid form to what appears to be a liquid state lacking a normal ACP SS structural form. The results for these experiments using various enzymes (carboxypeptidase W, chymopapain, bromelain, papain, ficin, licheninase, laminarinase, and β-(1→3)-D-glucanase, as well as other enzymes) to degrade ACP SSs are contained in Table 1 (above) under the "Sheath Degradation" column.

TABLE 4

| Enzyme/Supplier/EC # | Buffer | Concentration of enzyme in buffer in mg/ml, units/mL, or ratio (parts enzyme:parts buffer) | Conditions pH and Temp. |
|---|---|---|---|
| Flavourzyme ®* Sigma #P6110-50 mL EC #: 232-752-2 | 50 mM sodium phosphate | 1:10,000 | pH 7.0 Temp: 25° C. |
| Carboxypeptidase W Sigma #C6742 EC #: 3.4.16.6 | 50 mM sodium acetate | 2.0 units/mL | pH 4.46 Temp: 25° C. |
| Chymopapain Sigma #C8526-250UN EC #: 232-580-8 | 50 mM HEPES | 2.5 units/mL | pH 6.7 Temp: 25° C. |
| Bromelain Sigma B5144-100UN EC #: 253-387-5 | 50 mM HEPES | 1.42 units/mL | pH 6.7 Temp: 25° C. |
| Papain Sigma #P5306-25 mg EC #: 232-627-2 | 50 mM HEPES | 0.5 mg/mL | pH 6.7 Temp: 25° C. |
| Ficin Sigma #F6008 EC #: 232-599-1 | 50 mM HEPES | 0.1 mg/mL | pH 6.7 Temp: 25° C. |

*Flavourzyme ® is a protease cocktail (multiple-protease solution)

The proteases listed in Table 5 (infra) were then tested individually using the concentration and incubation conditions for each enzyme list in Table 5 to determine if each enzyme, individually, can prevent de novo formation of stylet sheaths in D. citri using the protocol set forth in Example 2, infra. D. citri diet feeding assays were constructed with diet containing carboxypeptidase W, bromelain, chymopapain, collagenase, ficin, papain, pepsin, or trypsin. Table 1 above indicates the observed effect of these proteases present in the diet on stylet sheath formation in the column labeled 'Inhibition of Sheath Formation'. Approximately 25 live *D. citri* adults were placed into polystyrene Cellstar 35 mm×10 mm dishes (Griener Bio-One, Monroe, N.C.), and a liquid ACP diet "sandwich" as describe above in Example 2 was used, substituting one of the proteases listed in Table 4 for cellulase and using 200 µl liquid ACP diet instead of 100 µl liquid ACP diet sandwiched between parafilm per MCF chamber. The chambers were incubated at a temperature of about 25° C., relative humidity of about 75%, and a light:dark cycle of about 14:10 hours. Sandwich diet chambers were maintained within clear Pyrex® baking dishes with the membrane (diet sandwich) side up, and the baking dish covered with a single layer of clear plastic wrap to prevent external contaminant interactions with the membrane surface during incubation. After approximately 24-hours incubation, the *D. citri* probing/feeding sites were observed using an inverted microscope. The results are listed in Table 1, column 'Inhibition of Sheath Formation'. Note, pepsin is not included in Table 1 because a control diet at pH 2.0 (the same optimal pH for pepsin degradation) showed inhibitory effects on sheath formation. Therefore, one was not able to distinguishable between pepsin and pH effects on stylet sheath formation. FIGS. 4E, 4F, 4G, and 4I are light micrographs of sites where *D. citri* fed on, or probed into, liquid diets containing carboxypeptidase W (FIG. 4E), chymopapain (FIG. 4F), bromelain (FIG. 4G), papain (FIG. 4H), and ficin (FIG. 4I). As shown in FIGS. 4E 4H, carboxypeptidase W, chymopapain, bromelain, and papain are capable of inhibiting the formation of ACP SSs because the sheaths were unable to form in the presence the enzyme tested. As shown in FIG. 4I, ficin appears to cause the abortion of *D. citri* feeding attempts because no sheath debris is visible in the diet when exposed to ficin. Trypsin and collagenase treatments did not appear to have an inhibitory effect on stylet sheath formation for Asian citrus psyllid (ACP).

TABLE 5

| Enzyme/Supplier/EC # | Stock Quantity | Percentage of Stock, Buffer, and Diet | Conditions pH and Temp. |
|---|---|---|---|
| Carboxypeptidase W<br>Sigma #: C6742<br>EC #: 3.4.16.6 | 2.8 mg/1 mL $H_2O$ | 25% Stock solution<br>25% Buffer (50 mM Sodium Acetate)<br>50% *D. citri* 2X diet | pH 4.46<br>Temp: 25° C. |
| Chymopapain<br>Sigma #: C8526-250UN<br>EC #: 232-580-8 | 10.2 mg/1 mL Sodium Acetate pH 6.2 | 25% Stock solution<br>25% Buffer (50 mM Sodium Acetate)<br>50% *D. citri* 2X diet | pH 6.2<br>Temp: 25° C. |
| Bromelain<br>Sigma #: B5144-100UN<br>EC #: 253-387-5 | 12.7 mg/1 mL $H_2O$ | 25% Stock solution<br>25% Buffer (50 mM HEPES)<br>50% *D. citri* 2X diet | pH 6.7<br>Temp: 25° C. |
| Papain<br>Sigma #: P5306-25 mg<br>EC #: 232-627-2 | 11.0 mg/1 mL $H_2O$ | 25% Stock solution<br>25% Buffer (50 mM HEPES)<br>50% *D. citri* 2X diet | pH 6.7<br>Temp: 25° C. |
| Ficin<br>Sigma #: F6008<br>EC #: 232-599-1 | 100 mg/1 mL $H_2O$ | 25% Stock solution<br>25% Buffer (50 mM HEPES)<br>50% *D. citri* 2X diet | pH 6.7<br>Temp: 25° C. |
| Trypsin<br>Sigma #: T8658-1VL<br>EC #: 232-650-8 | 100 ug/1 mL $H_2O$ | 25% Stock solution<br>25% Buffer (50 mM HEPES)<br>50% *D. citri* 2X diet | pH 6.7<br>Temp: 25° C. |
| Collagenase<br>Sigma #: C0773-1.5KU<br>EC #: 232-582-9 | 1 vial/1 mL $H_2O$ | 25% Stock solution<br>25% Buffer (50 mM HEPES)<br>50% *D. citri* 2X diet | pH 6.7<br>Temp: 25° C. |
| Pepsin<br>Sigma #: P6887-250 mg<br>EC #: 232-629-3 | 10.8 mg/1 mL $H_2O$ | 25% Stock solution<br>25% Buffer (10 mM HCL)<br>50% *D. citri* 2X diet | pH 2.0<br>Temp: 25° C. |

This example shows degradation of formed ACP SSs (see Table 1, "Sheath Degradation" column) and the complete prevention of de novo sheath formation (see FIGS. 4E 4H, and Table 1 "Sheath Inhibition" column) by carboxypeptidase W (FIG. 4E), chymopapain (FIG. 4F), bromelain (FIG. 4G), and papain (FIG. 4H), or the abortion of *D. citri* feeding attempts where no sheath debris is visible in the diet when exposed to ficin (FIG. 4I).

EXAMPLE 5

The effects of a protease (bromelain and ficin) contained within the previously described artificial diet (liquid ACP diet) were tested on the *Bemisia tabaci* biotype B whitefly (a Aleyrodidae, an SSFHI) using approximately 100 live *B. tabaci*. Approximately 100 live *B. tabaci* were placed into polystyrene Cellstar 35 mm×10 mm dishes (Griener Bio-One, Monroe, N.C.) using the liquid ACP diet "sandwich" described in Example 2, using approximately 200 μL liquid ACP diet with or without a protease using the conditions described in Table 6 below. The MFCs were incubated at a temperature of about 25° C., a relative humidity of about 75%, and a light:dark cycle of approximately 14:10 hours. MFCs were maintained within clear Pyrex® baking dishes with the membrane (liquid ACP diet "sandwich") side up, and the baking dish covered in a single layer of clear plastic wrap to prevent external contaminant interactions with the membrane surface during incubation. After about 24 hours incubation, the *B. tabaci* feeding sites were observed using an inverted microscope to see the effects of proteases in diet on the stylet sheaths for *B. tabaci*.

TABLE 6

| Enzyme/Source/EC # | Stock Quantity | Percentage of Stock and Diet | Conditions pH and Temp. |
|---|---|---|---|
| Bromelain Sigma #: B5144-100UN EC #: 253-387-5 | 20 units/1 mL of 50 mM HEPES | 50% stock solution 50% *D. citri* 2X diet (10 units final) | pH 6.7 Temp: 25° C. |
| Ficin Sigma #: F6008 EC #: 232-599-1 | 20 units/1 mL of 50 mM HEPES | 50% stock solution 50% *D. citri* 2X diet (10 units final) | pH 6.7 Temp: 25° C. |
| No enzyme (negative control) | 1 mL of 50 mM HEPES | 50% stock solution 50% *D. citri* 2X diet | pH 6.7 Temp: 25° C. |

FIG. 5A and FIG. 5B (enlargement of FIG. 5A) show a normal whitefly stylet sheath formed in the liquid ACP diet containing 50 mM HEPES (negative control). The use of 10 units of bromelain in 250 µl of liquid ACP diet resulted in the inhibition of stylet sheath formation for *B. tabaci* whiteflies as indicated in FIGS. 5C and 5D (enlargement of FIG. 5C). Using 10 units of ficin in 250 µl of liquid ACP diet (FIGS. 5E and 5F (enlargement of FIG. 5E) resulted in the inhibition of stylet sheath formation as well as reduced the number of whitefly feeding initiation sites.

The results indicate that *B. tabaci* stylet sheaths show a similar protease sensitivity profile to that observed in *D. citri*. Bromelain clearly prevents stylet sheath formation by *D. citri* and by *B. tabaci* in liquid ACP diet feeding chambers. Feeding initiation sites are typically evidenced by the flange material on the face of the feeding chamber; however, the face of the feeding chamber containing the liquid ACP diet and ficin lack the sheath shaft portion (see multiple aborted sites in FIG. 5C). Thus, it appears that ficin results in both a prevention of stylet sheath formation as well as a 'deterrent' like effect on initiation of feeding sites by these insects. In the presence of sheath-shaft degrading enzymes, no further sheath polymerization is observed aside from the flange. In the presence of ficin, not only is shaft formation inhibited, but initiation of feeding sites (appearance of flange deposition) is reduced. These results indicate that bromelain and ficin have similar inhibitory effects on salivary sheath formation in psyllids and whiteflies, and therefore strategies deploying the use of stylet sheath formation inhibitors described herein should function against these and other salivary sheath forming hemipteran insects.

After performing the experiments using liquid ACP diet containing either bromelain or ficin experiment on *B. tabaci*, a similar experiment is performed substituting BAPN for the enzyme. For this experiment, the concentration of BAPN in water at 50 mM; all other conditions are identical to the conditions listed in Table 6. Upon examining the *B. tabaci* feeding sites on the membrane using an inverted microscope, it was evident that BAPN also prevents stylet sheath formation in *B. tabaci*.

EXAMPLE 6

Bromelain and ficin were tested to determine if they can deter or prevent *D. citri* from feeding on treated citrus leaf surfaces. Single excised leaf assays were performed using single leaves from *Citrus macrophylla* that were washed extensively with filtered sterilized diH$_2$O (3x) to clean any potential surface chemical contaminants from the leaves that could confound the results. The leaves were then dried and divided into three groups. For the first group, negative control, the leaves were drenched by dunking into an approximately 50 mM HEPES solution. For the second group, the leaves were dunked into an approximately 50 mM HEPES solution containing approximately 1 unit/ml ficin. The leaves in the third group were dunked into an approximately 50 mM HEPES solution containing approximately 1 unit/ml ficin and approximately 1 unit/ml bromelain. The leaves in each group were air dried and placed in individual 50 mL conical tubes (replicated in triplicate). Approximately 50 *D. citri* were placed in each tube, the tubes were capped with a mesh screen cap, and the adult *D. citri* were allowed to feed for approximately 24 hours under standard testing conditions of approximately 25° C., approximately 75% relative humidity, and a light:dark cycle of approximately 14:10 hours in a walk-in incubator chamber.

FIGS. 6A 6F are scanning electron micrographs (SEM) images of *Citrus macrophylla* leaf surfaces on which *D. citri* adults were allowed to feed. FIGS. 6A and 6B are *C. macrophylla* leaf surface that were treated only with water prior to feeding (negative controls) on which normal stylet flange formation can be seen (highlighted by brackets) which indicates normal feeding by *D. citri*. FIGS. 6C and 6D are SEM images of ficin treated *C. macrophylla* leaf surfaces and show 'non-typical' stylet flange formation (see bracket areas) compared to the negative control leaves (see FIGS. 6A and 6B). FIGS. 6E and 6F are SEM images of the ficin and bromelain treated *C. macrophylla* leaf surfaces and show 'highly-deformed' stylet flanges (see bracket areas) compared to negative control leaves (see FIGS. 6A and 6B). The number of feeding attempts by *D. citri* on both the ficin only treated leaves and the ficin and bromelain treated leaves are reduced compared to the number of feeding attempts on the negative control leaves, as indicated by a dramatic reduction in the quantity of *D. citri* flanges or stylet 'flange-like' on the protease treated leaves. The number of feeding sites observed on the protease treated leaves were less than 10% of the number of feeding sites observed on the negative control leaves.

This example indicates that proteases applied onto leaves can reduce *D. citri* feeding on the treated leaves.

EXAMPLE 7

Stylet sheath composition and structure information is useful information used to identify stylet sheath inhibiting molecules that can be used as feeding inhibitors. The ability to isolate quantities of pure sheaths allowed various types of compositional and structural analysis to be performed. Sugar composition and linkage analysis of neutral and uronic acid sugars was performed by converting Proteinase K solubilized Solvy™ membrane isolated ACP SS samples to partially methylated alditol acetates (PMAAs) (Cucianu and Kerek, Carbohydr. Res., 131, 209-217, 1984) and analysing the products by GC/MS. Briefly, the sample was hydrolyzed with 2M TFA at 120° C. for 4 hours followed with permethylation and conversion to alditol acetates (AA).

To obtain ACP SSs for PMAA and subsequent NMR analysis, ACPs were placed into MFCs covered with Solvy™ stabilizer membrane (Sulky®, Kennesaw, Ga.) and were allowed to deposit fully formed SSs across the Solvy™ stabilizer membranes as they attempted to feed. These MFC membranes were then collected and washed with approximately 100% ethanol (Aaper, Shelbyville, Ky.) to remove debris. These ethanol-cleaned membranes with attached salivary sheaths were then placed into approximately 50 ml of sterile filtered (0.2 μm) deionized $H_2O$ to dissolve the water-soluble Solvy™ membranes. As the membranes dissolved, a slurry of water, dissolved Solvy™, and fully formed ACP SSs was generated. This slurry was then filtered a 5 μm filter to remove Solvy™ components and excess $H_2O$; the fully formed ACP SSs collected on the filter. This filter was then washed with 50 ml of approximately 100% ethanol so that the ACP SSs and ethanol were collected in a sterile 50 mL conical tube. The ACP SSs were then centrifuged at 12×g for 10 minutes, and supernatant ethanol was removed via suction. A minimal amount of ethanol remained (approximately 25 μl), and the excess ethanol was allowed to evaporate from the ACP SS pellet using a centrifugal vacuum evaporator on low heat for less than approximately 30 minutes resulting in fully formed (dry) ACP SSs in the conical tube.

To degrade proteins associated with the ACP SSs, and as a result dissolve the SSs, a minimal quantity of proteinase K (10 μg) (Thermo Fisher Scientific, Inc., Waltham, Mass.) in 1 ml of deionized nanopure $H_2O$ was added to 1 mg of collected, dried ACP SSs, and this mixture was incubated overnight at 55° C. Following the overnight protein digestion, proteinase K was then deactivated by heating the ACP SS/proteinase K solution at 75° C. for 1 hour. The sample was then lyophilized to a dry powder. Following lyophilization, the crude proteinase K treated ACP SSs was suspended in deionized water to approximately 1 mg/mL and dialyzed against 4 L of deionized $H_2O$ using a 1,000 molecular weight cut off dialysis bag (Spectrum Laboratories, Inc., Rancho Dominguez, Calif.) to remove (or greatly reduce) salts and amino acid monomers.

Subsequent GC/MS analysis of PMAA treated sheath material provided composition information indicating that the ACP SS contained a predominance of glucose (~90% of total carbohydrate identified) and smaller quantities of mannose and xylose. Linkage analysis showed that the main sugar residue identified was 4-linked Glcp (82%) (p=pyranose form of the sugar; e.g., 'Glcp' is the pyranose form of glucose. Branching (4,6-Glcp (4%) and 3,4-Glcp) and terminal Glcp (3%) were also observed. Finally small amounts of 4-Manp (4%) and 4-Xylp (4%) were also observed. These finding indicate the predominance of glucose as the structural sugar monomer and the presence of only carbon-4 bonding supports the predominance of 1,4 linked glucose (C-1 bonding cannot be distinguished with this method). Interestingly a small amount of 4,6 and 3,4 branched glucose was also present indicating a more complicated structure than just linear 1,4-linked glucose. Verification of glucose bonds and determination of the bond orientation linkages of the 1→4 Glcp bonds was made by comparing the 1D NMR spectra of the proteinase K treated ACP SSs to the 1D NMR spectra of other known compounds having known bond linkages. These findings indicated that the ACP SSs contained bonds indicative of a glycogen-like molecule (Sillerud and Shulman, Biochemistry Volume 22(5): 1087-1094, 1983; Zang, Rothman, et al., Proceedings of the National Academy of Sciences of the United States of America Volume 87(5): 1678-1680, 1990; Zang, Howseman, et al., Carbohydrate Research Volume 220(0): 1-9, 1991). See FIG. 8.

To verify the data from PMAA analysis and the structure, ACP SS preparation 1D proton and 2D (COSY, TOCSY, NOESY and $^1H$—$^{13}C$—HMQC) experiments were performed as previously described in Sillerud and Shulman, Biochemistry, Volume 22(5), 1087-1094, 1983; and Zang et al., Proceedings of the National Academy of Sciences of the United States of America, Volume 87(5), 1678-1680, 1990. The dialyzed sample and a non-dialyzed sample of the lyophilized proteinase K-digested ACP SSs was dissolved in water to approximately 1 mg/mL and was exchanged twice with 99.9 atom % D (Deuterium oxide—$D_2O$, Cambridge Isotope Laboratories, Andover, Mass.) to remove $H_2O$ from the sample, and then the exchanged sample was finally dissolved in 100 atom % $D_2O$ (Cambridge Isotope Laboratories, Andover, Mass.). 1D-proton spectra were acquired at both 25° C. and 70° C. and then 2D proton spectra analysis (correlation spectroscopy, COSY; total correlation spectroscopy, TOCSY; nuclear Overhauser effect spectroscopy, NOESY; and $^1H$—$^{13}C$ heteronuclear multiple-quantum correlation, $^1H$—$^{13}C$—HMQC) at 70° C. All analyses were performed on a Varian 600 MHz NMR spectrometer (Agilent, Inc., Palo Alto, Calif.). For the 2D acquisitions, the residual water signal was suppressed using the standard Agilent 'PRESAT' pulse sequence, which applies selective 1 s pulse suppression at the HDO frequency with low field strength of 10 Hz. Spectra were processed using MestReC Nova software (Mestrelab Research, Santiago de Compostela, Spain).

Initial 1D NMR proton spectra of ACP SSs before and after Proteinase K treatment revealed the likely presence of protein and/or peptides and/or free amino acids. These signals were significantly reduced when the Proteinase K treated sample was dialyzed against deionized water as described above. This finding of proteinase K sensitive material supports the concept that proteins are a structural component of the ACP SSs.

The ACP SS preparation 1D proton and 2D (COSY, TOCSY, NOESY and $^1H$—$^{13}C$—HMQC) experiments revealed that major component of the analyzed polymer is α-(1→4)-Glcp (see FIG. 8, FIGS. 9A 9E and FIGS. 10A 10E). The proton NMR spectrum indicated the presence of one major resonance at δ5.32 ppm in the anomeric region and non-anomeric signals because of ring system protons (3.59-3.91 ppm). The 1D spectrum was identical to spectra reported in the past for glycogen (see, Sillerud and Shulman, Biochemistry, Volume 22(5), 1087-1094, 1983; Zang et al., Proceedings of the National Academy of Sciences of the United States of America, Volume 87(5), 1678-1680, 1990; Zang, et al., Carbohydrate Research Volume 220(0), 1-9, 1991; and Biological Magnetic Resonance Data Bank (www.bmrb.wisc.edu/metabolomics/mol_summary/spectrum_display.php?title=1D %201H&mol_dir=glycogen&exp=1H&mol=Glycogen&bmrbid=bmse000232&pH=7.4), a predominantly glucose α-(1→4)-linked polymer with periodic α-(1→6)-branching.

These 2D proton and proton-carbon experiments assigned major resonances for the protons and their corresponding carbons. Proton and carbon chemical shifts of major chemical resonance found in ACP SS acquired at 70° C. are given in Table 7 infra. These chemical shifts are similar to those previously reported for α-(1→4)-Glcp and is again consistent with glycogen. The 1→4 linkage between Glc residues was observed inter-residue NOE-connectivity and the cross peak of H1-H4 at 65.32/3.60 (FIG. 10C). This connectivity was also overlapping with intra-residue interaction of H1-H2; 65.32/3.59. Minor signals in the NMR spectra were observed that likely originate from branching 4.6-Glcp residue. The complete assignment for 1→6 linked branching Glc was not made at this stage as it gives very low response in NMR experiment. In the linkage analysis only 3% of 4.6-Glcp was found. Some signals originating from β-linked sugar that likely originate from 4-Manp were also observed; however, because 4-Manp is not major component, tracing of that signal in NMR was difficult.

TABLE 7

| Residue | 1 | 2 | 3 | 4 | 5 | 6 |
| --- | --- | --- | --- | --- | --- | --- |
| A-(1→4)-Glcp | 5.32 (100) | 3.59 (71.75) | 3.91 (73.78) | 3.60 (77.84) | 3.78 (71.75) | 3.88/3.84 (61.08) |

In summary, based on the composition, linkage, and NMR analysis, the carbohydrate component is approximately 90% α-(1-4)-glucan polymer with approximately 3% branching at the 6-position and an apparent small percentage of beta-linked glucan. The remainder of the carbohydrate consists of mannose and xylose, but the structure of those components is not known.

EXAMPLE 8

The small molecules listed in Table 8 are "generally regarded as safe" (GRAS) and are naturally present in citrus fruit. An amount is indicated for each GRAS small molecule in Table 8 that was weighed out and to this amount approximately 100 μl of about 10% ethanol was added to aid in solubilization of the respective GRAS small molecule. Subsequently, about 900 μl $H_2O$ was added to each of the ethanol/GRAS small molecules. Liquid ACP diet was prepared as described above in Example 2. A quantity of liquid ACP diet with GRAS small molecule was combined to form about 175 μl of liquid ACP diet containing individual GRAS small molecules at the concentration indicated in Table 8 for testing their effect on ACP feeding and stylet sheath formation. Approximately 25 D. citri were collected into polystyrene Cellstar 35 mm×10 mm dishes (Griener Bio-One, Monroe, N.C.) that were then sealed using a single layer of Parafilm® M (Pechiney Plastic Packaging Company, Chicago, Ill.). Approximately 175 μl of liquid ACP diet with the respective individual GRAS small molecule were used to make an MFC "sandwich" (e.g., Parafilm® M—liquid ACP diet with GRAS small molecules—Parafilm® M) as described in Example 2 which cover a Petri dish containing ACP. This MFC was then incubated at about 25° C., at about 75% relative humidity, with a light:dark cycle of approximately 14:10 hours for a period of about 24 hours. After about 24 hours, for each MFC the stylet sheaths were observed using an inverted microscope. The effects of each GRAS small molecule used in diet against ACP stylet sheath formation is provided in Table 8. FIG. 11A shows the malformations observed when eriocitrin was added to the diet resulting in malformation of sheaths. FIG. 11B shows the inhibition of flange solidification when nomilin was added to the diet.

TABLE 8

| GRAS Small Molecules | Mol/ Weight (g/mol) | Concentration (mM) in 175 μL of liquid ACP diet | Effect |
| --- | --- | --- | --- |
| Hesperidin | 610.56 | 2.62 | No Effect |
| Naringin | 580.53 | 2.76 | Malformed sheaths |
| Didymin | 594.56 | 1.51 | Malformed sheaths |
| Eriodictyol | 288.25 | 3.47 | Malformed sheaths |
| Eriocitrin | 596.53 | 1.68 | Malformed sheaths |
| Hesperetin | 302.27 | 3.64 | Malformed sheaths |
| Naringenin | 272.26 | 3.31 | Malformed sheaths |
| 7-HO-Coumarin | 162.14 | 8.02 | Malformed sheaths |
| Limonin | 470.52 | 2.55 | Malformed sheaths |
| Limonin glucoside | 650.67 | 1.69 | Malformed sheaths |
| Nomilin | 514.56 | 2.53 | Flange liquefied, sheath was normal |

In summary, the results presented herein illustrate that it is possible to reduce or even prevent feeding on plants of stylet sheath forming plant-feeding hemipterans using a strategy that is effective on all or many stylet sheath forming plant-feeding hemipterans. Thus, one could use the compositions and methods of this invention to prevent or reduce damage to economically important plants caused by stylet sheath forming plant-feeding hemipterans.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention. All references cited herein are incorporated by reference.

We, the inventors, claim:

1. A method of preventing formation of a hemipteran insect's stylet sheath comprising applying to a plant a composition in an amount effective to prevent formation of said hemipteran insect's stylet sheath, wherein said composition comprises an agriculturally acceptable carrier, at least one compound effective in preventing formation of said hemipteran insect's stylet sheath, and optionally an adjuvant, wherein said compound is selected from the group consisting of (i) at least one carbohydrate-degrading enzyme that prevents stylet sheath formation, (ii) at least one protease that prevents stylet sheath formation, (iii) at least one small molecule that prevents stylet sheath formation, and (iv) a combination thereof.

2. The method of claim 1 wherein said protease is selected from the group consisting of cellulase, protease from Aspergillus oryzae, carboxypeptidase, chymopapin, papain, bromelain, ficin, proteinase K, calpain, caspase, cathepsin, actinidin, tobacco etch virus protease, γ-glutamyl hydrolase, and a combination thereof.

3. The method of claim 1 wherein said carbohydrate-degrading enzyme is selected from the group consisting of amyloglucosidase, α-amylase, laminarinase, licheninase, cellulase, hemicellulase, glucuronyl hydrolase, lytic polysaccharide monooxygenase, β-1,4-endoglucanase, endo-1,3 (4)-β-glucanases, endodextranase, xylanase, mannan-degrading hydrolase, and a combination thereof.

4. The method of claim 1 wherein said small molecule is selected from the group consisting of 3-aminopropionitrile fumarate salt, dithiothreitol solution, nitrilotriacetic acid trisodium salt, 4-hydroxybenzyl alcohol, kojic acid, ammonium tetrathiomolybdate, ethylenediaminetetraacetic acid (EDTA), D-penicillamine, 2,3,2-tetramine, 2,2,2-tetramine, 1,4,8,11-tetraazacyclotetradecane-1,4,8,11-tetraacetic acid (TETA), N,N',N"-tris(2-pyridylmethyl)-1,3,5-cis,cis,-triaminocyclohexane (tachpyr), naringin, didymin, eriodictyol, eriocitrin, hesperetin, naringenin, 7-hydroxy-coumarin, limonin, limonin glucoside, nomilin, and a combination thereof.

5. The method of claim 1 wherein said small molecule is a copper chelating agent or a laccase inhibitor.

6. The method of claim 1 wherein said adjuvant is selected from the group consisting of at least one buffer, at least one penetrating agent, at least one surfactant, at least one oil, at least one humectant, and a combination thereof.

7. A method of degrading a hemipteran insect's stylet sheath comprising applying to a plant a composition in an amount effective to degrade said hemipteran insect's stylet sheath, wherein said composition comprises an agriculturally acceptable carrier, at least one compound effective in degrading said hemipteran insect's stylet sheath, and optionally an adjuvant, wherein said compound is selected from the group consisting of (i) at least one carbohydrate-degrading enzyme that degrades stylet sheath, (ii) at least one protease that degrades stylet sheath, (iii) at least one small molecule that that degrades stylet sheath, and (iv) a combination thereof.

8. The method of claim 7 wherein said protease is selected from the group consisting of cellulase, protease from *Aspergillus oryzae*, carboxypeptidase, chymopapin, papain, bromelain, ficin, proteinase K, calpain, caspase, cathepsin, actinidin, tobacco etch virus protease, γ-glutamyl hydrolase, and a combination thereof.

9. The method of claim 7 wherein said carbohydrate-degrading enzyme is selected from the group consisting of amyloglucosidase, α-amylase, laminarinase, licheninase, cellulase, hemicellulase, glucuronyl hydrolase, lytic polysaccharide monooxygenase, β-1,4-endoglucanase, endo-1,3(4)-β-glucanases, endodextranase, xylanase, mannan-degrading hydrolase, and a combination thereof.

10. The method of claim 7 wherein said small molecule is selected from the group consisting of 3-aminopropionitrile fumarate salt, dithiothreitol solution, nitrilotriacetic acid trisodium salt, 4-hydroxybenzyl alcohol, kojic acid, ammonium tetrathiomolybdate, ethylenediaminetetraacetic acid (EDTA), D-penicillamine, 2,3,2-tetramine, 2,2,2-tetramine, 1,4,8,11-tetraazacyclotetradecane-1,4,8,11-tetraacetic acid (TETA), N,N',N"-tris(2-pyridylmethyl)-1,3,5-cis,cis,-triaminocyclohexane (tachpyr), naringin, didymin, eriodictyol, eriocitrin, hesperetin, naringenin, 7-hydroxy-coumarin, limonin, limonin glucoside, nomilin, and a combination thereof.

11. The method of claim 7 wherein said small molecule is a copper chelating agent or a laccase inhibitor.

12. The method of claim 7 wherein said adjuvant is selected from the group consisting of at least one buffer, at least one penetrating agent, at least one surfactant, at least one oil, at least one humectant, and a combination thereof.

13. A method for reducing or preventing transmission of a vascular associated disease to a plant from a hemipteran insect that is a carrier of bacteria, viruses, or microorganisms that cause said vascular associated disease comprising applying to said plant an agriculturally acceptable carrier, at least one compound in an amount effective to reduce or prevent said hemipteran insect from feeding on said plant, and optionally an adjuvant, wherein said compound is selected from the group consisting of (i) at least one carbohydrate-degrading enzyme that prevents stylet sheath formation and/or degrades stylet sheath formation, (ii) at least one protease that prevents stylet sheath formation and/or degrades stylet sheath formation, (iii) at least one small molecule that prevents stylet sheath formation and/or degrades stylet sheath formation, and (iv) a combination thereof, and wherein said reduction or prevention of feeding of said hemipteran insect on said plant results in said reducing or prevention of transmission of said bacteria, viruses, or microorganisms that cause said vascular associated disease.

14. The method of claim 13 wherein said protease is selected from the group consisting of cellulase, protease from *Aspergillus oryzae*, carboxypeptidase, chymopapin, papain, bromelain, ficin, proteinase K, calpain, caspase, cathepsin, actinidin, tobacco etch virus protease, γ-glutamyl hydrolase, and a combination thereof.

15. The method of claim 13 wherein said carbohydrate-degrading enzyme is selected from the group consisting of amyloglucosidase, α-amylase, laminarinase, licheninase, cellulase, hemicellulase, glucuronyl hydrolase, lytic polysaccharide monooxygenase, β-1,4-endoglucanase, endo-1,3(4)-β-glucanases, endodextranase, xylanase, mannan-degrading hydrolase, and a combination thereof.

16. The method of claim 13 wherein said small molecule is selected from the group consisting of 3-aminopropionitrile fumarate salt, dithiothreitol solution, nitrilotriacetic acid trisodium salt, 4-hydroxybenzyl alcohol, kojic acid, ammonium tetrathiomolybdate, ethylenediaminetetraacetic acid (EDTA), D-penicillamine, 2,3,2-tetramine, 2,2,2-tetramine, 1,4,8,11-tetraazacyclotetradecane-1,4,8,11-tetraacetic acid (TETA), N,N',N"-tris(2-pyridylmethyl)-1,3,5-cis,cis,-triaminocyclohexane (tachpyr), naringin, didymin, eriodictyol, eriocitrin, hesperetin, naringenin, 7-hydroxy-coumarin, limonin, limonin glucoside, nomilin, and a combination thereof.

17. The method of claim 13 wherein said small molecule is a copper chelating agent or a laccase inhibitor.

18. The method of claim 13 wherein said adjuvant is selected from the group consisting of at least one buffer, at least one penetrating agent, at least one surfactant, at least one oil, at least one humectant, and a combination thereof.

* * * * *